US010925606B2

(12) United States Patent
Friedman et al.

(10) Patent No.: US 10,925,606 B2
(45) Date of Patent: Feb. 23, 2021

(54) TENDON REPAIR APPARATUS

(71) Applicants: Guy Friedman, Ashkelon (IL); Hagar Patish, Ganei-Yehuda (IL); Yossi Suzer, Rishon-LeZion (IL)

(72) Inventors: Guy Friedman, Ashkelon (IL); Hagar Patish, Ganei-Yehuda (IL); Yossi Suzer, Rishon-LeZion (IL)

( * ) Notice: Subject to any disclaimer, the term of this patent is extended or adjusted under 35 U.S.C. 154(b) by 98 days.

(21) Appl. No.: 15/303,821

(22) PCT Filed: Apr. 13, 2014

(86) PCT No.: PCT/IL2014/050361
§ 371 (c)(1),
(2) Date: Oct. 13, 2016

(87) PCT Pub. No.: WO2015/159277
PCT Pub. Date: Oct. 22, 2015

(65) Prior Publication Data
US 2017/0027578 A1    Feb. 2, 2017

Related U.S. Application Data

(63) Continuation-in-part of application No. 14/053,757, filed on Oct. 15, 2013, now Pat. No. 9,877,713.
(Continued)

(51) Int. Cl.
*A61B 17/11* (2006.01)
*A61B 17/064* (2006.01)
*A61B 17/00* (2006.01)

(52) U.S. Cl.
CPC ........ *A61B 17/1146* (2013.01); *A61B 17/064* (2013.01); *A61B 17/0643* (2013.01);
(Continued)

(58) Field of Classification Search
CPC ... A61B 17/04; A61B 17/064; A61B 17/0643; A61B 17/0644; A61B 17/068;
(Continued)

(56) References Cited

U.S. PATENT DOCUMENTS 4,738,062 A    4/1988 Dickey
5,053,047 A *  10/1991 Yoon .................. A61B 17/0469
                                              606/223
(Continued)

FOREIGN PATENT DOCUMENTS

EP           1221909        7/2002
WO        WO 01/76488      10/2001
WO       WO 2015/159277    10/2015

OTHER PUBLICATIONS

Applicant-Initiated Interview Summary dated Aug. 18, 2016 From the US Patent and Trademark Office Re. U.S. Appl. No. 14/053,757.
(Continued)

*Primary Examiner* — Kathleen S Holwerda
*Assistant Examiner* — Kankindi Rwego

(57) ABSTRACT

An apparatus for coupling two elongated tissue portions of a subject, such as two portions of a ruptured tendon, comprising first and second repair elements, each repair element comprising a distal end configured for insertion into the tissue portion, an elongated body configured to extend axially within the tissue portion and to engage the tissue, and a proximal end. In some embodiments, at least one of the first and second repair elements comprises, at the proximal end, an integrally formed connector for coupling the proximal end of the first repair element to a proximal end of the second repair element, to attach between the two tissue portions.

21 Claims, 18 Drawing Sheets

Related U.S. Application Data

(60) Provisional application No. 61/713,689, filed on Oct. 15, 2012.

(52) U.S. Cl.
CPC ........... *A61B 2017/00477* (2013.01); *A61B 2017/0641* (2013.01); *A61B 2017/0647* (2013.01); *A61B 2017/0649* (2013.01); *A61B 2017/1132* (2013.01)

(58) Field of Classification Search
CPC ............ A61B 17/072; A61B 17/07207; A61B 2017/00477; A61B 2017/0641; A61B 2017/0647; A61B 2017/0648; A61B 2017/0649; A61B 17/11; A61B 17/1114; A61B 17/1128; A61B 17/1146; A61B 17/115; A61B 17/1152; A61B 17/1155; A61B 17/12; A61B 2017/1103; A61B 2017/1107; A61B 2017/111; A61B 2017/1117; A61B 2017/1121; A61B 2017/1125; A61B 2017/1132; A61B 2017/1142; A61B 2017/1157

See application file for complete search history.

(56) References Cited

U.S. PATENT DOCUMENTS

| | | | |
|---|---|---|---|
| 5,591,206 A | 1/1997 | Moufarrege | |
| 5,810,851 A | 9/1998 | Yoon | |
| 6,663,633 B1 | 12/2003 | Pierson, III | |
| 6,712,830 B2 | 3/2004 | Esplin | |
| 6,984,241 B2 | 1/2006 | Lubbers et al. | |
| 7,959,648 B2 | 6/2011 | Mas | |
| 8,062,363 B2 | 11/2011 | Hirpara et al. | |
| 2003/0014077 A1* | 1/2003 | Leung | A61B 17/04 606/228 |
| 2007/0038221 A1 | 2/2007 | Fine et al. | |
| 2007/0225737 A1 | 9/2007 | Messerly et al. | |
| 2008/0082130 A1 | 4/2008 | Ward | |
| 2008/0108989 A1 | 5/2008 | Parsell et al. | |
| 2009/0069822 A1 | 3/2009 | Takahashi et al. | |
| 2009/0216252 A1* | 8/2009 | Melvin | A61B 17/0057 606/151 |
| 2009/0306681 A1* | 12/2009 | Del Nido | A61B 17/0401 606/139 |
| 2011/0009902 A1 | 1/2011 | Leung et al. | |
| 2012/0109193 A1* | 5/2012 | Primavera | A61B 17/06166 606/228 |
| 2012/0330327 A1 | 12/2012 | McClellan | |
| 2014/0114351 A1 | 4/2014 | Friedman et al. | |

OTHER PUBLICATIONS

International Preliminary Report on Patentability dated Oct. 27, 2016 From the International Bureau of WIPO Re. Application No. PCT/IL2014/050361.

International Search Report and the Written Opinion dated Jan. 14, 2015 From the International Searching Authority Re. Application No. PCT/IL2014/050361.

Invitation to Pay Additional Fees dated Nov. 13, 2014 From the International Searching Authority Re. Application No. PCT/IL2014/050361.

Official Action dated Apr. 23, 2015 From the US Patent and Trademark Office Re. U.S. Appl. No. 14/053,757.

Official Action dated Feb. 25, 2016 From the US Patent and Trademark Office Re. U.S. Appl. No. 14/053,757.

Merriam-Webster's "Crimp", Merriam-Webster's Learner's Dictionary, Definition for English-Language Learners, 2 Pages, 2015.

Official Action dated Feb. 10, 2017 From the US Patent and Trademark Office Re. U.S. Appl. No. 14/053,757. (6 pages).

* cited by examiner ated filing date of Apr. 13, 2014, which is a Continuation-in-Part
TENDON REPAIR APPARATUS

RELATED APPLICATIONS

This application is a National Phase of PCT Patent Application No. PCT/IL2014-1050361 having International filing date of Apr. 13, 2014, which is a Continuation-in-Part (CIP) of U.S. patent application Ser. No. 14/053,757 filed on Oct. 15, 2013, which claims the benefit of priority under 35 USC § 119(e) of U.S. Provisional Patent Application No. 61/713,689 filed on Oct. 15, 2012

This application is also a Continuation-in-Part (CIP) of U.S. patent application Ser. No. 14/053,757 filed on Oct. 15, 2013, which claims the benefit of priority under 35 USC §119(e) of U.S. Provisional Patent Application No. 61/713, 689 filed on Oct. 15, 2012.

The contents of the above applications are incorporated herein by reference in their entirety.

FIELD OF THE INVENTION

Applications of the present invention relate generally to tissue repair, and specifically to implantable medical devices for facilitating tendon repair.

BACKGROUND

Tendon rupture is painful, and may cause reduction or loss of movement in an affected tendon tract and/or one or more joints. Typically, a ruptured tendon is repaired surgically, using sutures, in either an open or a percutaneous procedure. Alternatively, the tendon is not repaired surgically. Tendon rupture is typically more prevalent in males.

SUMMARY OF THE INVENTION

According to an aspect of some embodiments there is provided an apparatus for coupling two elongate tissue portions of a subject, comprising: a first and second repair elements, each repair element comprising a distal end configured for insertion into the tissue portion, an elongated body configured to extend axially within the tissue portion and to engage the tissue, and a proximal end; at least one of the first and second repair element comprising, at the proximal end, an integrally formed connector for coupling the proximal end of the first repair element to a proximal end of the second repair element, to attach between the two tissue portions. In some embodiments, each of the repair elements comprises a connector at its proximal end, the connectors shaped with matching profiles to connect to each other. In some embodiments, the connectors at the proximal ends of the repair elements comprise a female connector formed with a plurality of slots, and a male connector formed with a plurality of tabs configured to snap into the slots of the female connector upon connection. In some embodiments, the connectors at the proximal ends of the repair elements comprise a female connector and a male connector, the male connector comprising a projection and the female connector comprising a recess, the projection and recess formed with matching profiles suitable for defining an orientation of the first repair element with respect to the second repair element. In some embodiments, connectors at the proximal ends of the repair elements comprise a female connector configured for receiving a male connector, the female connector comprising one or more axially extending slots to be elastically deformed when receiving a projection of the male connector. In some embodiments, a first connector projects externally to a proximal end of the first tissue portion, and a second connector is embedded within a proximal end of the tissue portion, to overlap each other when connected. In some embodiments, the connector is positioned at an axial location with respect to the elongate tissue portion. In some embodiments, the connector is positioned at a non-axial location with respect to the elongate tissue portion. In some embodiments, the repair element is shaped as a helix. In some embodiments, each of the repair elements comprises a plurality of axially extending strands configured to engage the elongate tissue portion, the strands arranged in a cylindrical configuration. In some embodiments, the strands are formed of a shape memory alloy. In some embodiments, the strands are winded with respect to a longitudinal axis of the repair element. In some embodiments, the strands occupy between 5% and 25% of a cross sectional area of the tissue. In some embodiments, the strands comprise elastic distal ends to be bended in a proximal direction for penetrating into the tissue. In some embodiments, at least the second repair element is a helical element; and a connector configured at a proximal end of the first repair element comprises a shaft formed with a recess having a circular profile for receiving a proximal end of the helical second element. In some embodiments, the connector is elastic enough to enable flexing of the tissue portions when connected to each other. In some embodiments, a diameter of the connector is smaller than a diameter of the tissue portion by at least 10%.

According to an aspect of some embodiments of the invention there is provided a delivery device for use with a tissue repair apparatus, comprising: a shaft comprising a tissue repair element positioned at a distal portion of the shaft, a knob at a proximal end of the shaft, the knob engageable by a user, an elastic element configured between the tissue repair element and the knob, the elastic element transferring force from a direction of the knob to the tissue repair element to force the tissue repair element out a distal opening of the shaft, the repair element advancable within the shaft by step-wise clicking of the knob by the user. In some embodiments, a tissue repair kit is provided, comprising two delivery devices for example as described herein, each delivery device for use with one of two tissue portions intended to be coupled to each other. In some embodiments, the delivery device is disposable.

According to an aspect of some embodiments of the invention there is provided a gripping device for use with a tissue repair apparatus, comprising a first portion configured to encompass a first tissue portion; a second portion configured to encompass a second tissue portion; the first portion of the device received within the second portion of the device to form a sleeve like configuration, bringing the tissue portions closer to each other and holding them in place; wherein each of the portions of the device is configured to hold one of the tissue portions at a distance of at least 0.5 cm from an end of the tissue portion, the distance sufficient for attaching the two ends of the tissue portions to each other. In some embodiments, the gripping device comprises one or more windows for accessing the proximal ends of the tissue portions.

According to an aspect of some embodiments of the invention there is provided a method for repairing damaged tissue of a subject, comprising identifying a rupture in the tissue, introducing a first repair element into a first tissue portion on a first side of the rupture, introducing a second repair element into a second tissue portion on an opposing side of the rupture, approximating the proximal ends of the first and second tissue portions, and connecting the first and second repair elements together to reduce a gap at the rupture. In some embodiments, the damaged tissue is a ruptured tendon. In some embodiments, the method further comprises verifying linear movement of the tendon. In some embodiments, connecting comprises crimping the locking element to fasten the connection. In some embodiments, connecting comprises at least one of aligning the first and second repair elements, and setting an orientation of the first and second repair elements with respect to each other.

According to an aspect of some embodiments of the invention there is provided an apparatus that comprises two helical elements, configured to be coupled to respective portions of at least one tissue, and to subsequently be coupled to each other, thereby coupling together the two portions of the tissue. Typically, the helical elements are configured to be lockably coupled to each other. Typically, the helical elements are configured to be coupled to exposed ends of a transected tendon by being screwed into the exposed ends, and the apparatus is configured to facilitate repair of the tendon.

There is therefore provided, in accordance with an application of the present invention, apparatus for use with at least one tissue of a subject, the apparatus including:

a first helical element, configured to be coupled to a first portion of the tissue of the subject;

a second helical element, configured to be coupled to a second portion of the tissue of the subject; and a locking element, configured, following the coupling of the first and second helical elements to the first and second portions of the tissue, to couple the first helical element to the second helical element such that the first and second helical elements are collinear.

In an application, the locking element is configured to lockably couple the first helical element to the second helical element.

In an application, no portion of the locking element includes suture.

In an application, the locking element includes suture.

In an application, the two helical elements are shaped to have the same handedness.

In an application, the apparatus is configured to inhibit an increase in a distance between the first and second portions of the tissue when (1) the first helical element is coupled to the first portion of the tissue, and (2) the second helical element is coupled to the second portion of the tissue and is lockably coupled by the locking element to the first helical element.

In an application:

the first portion of the tissue of the subject includes a first portion of a damaged tissue of the subject, the second portion of the tissue of the subject includes a second portion of the damaged tissue of the subject, and the apparatus is configured to facilitate repair of the damaged tissue of the subject.

In an application:

the damaged tissue includes a transected blood vessel of the subject, and the apparatus is configured to facilitate repair of the transected blood vessel by being configured to inhibit an increase in a distance between first and second portions of the transected blood vessel.

In an application:

the damaged tissue includes a transected ureter of the subject, and the apparatus is configured to facilitate repair of the transected ureter by being configured to inhibit an increase in a distance between first and second portions of the transected ureter.

In an application:

the damaged tissue includes a transected urethra of the subject, and the apparatus is configured to facilitate repair of the transected urethra by being configured to inhibit an increase in a distance between first and second portions of the transected urethra.

In an application:

the damaged tissue includes a transected tendon of the subject, and the apparatus is configured to facilitate repair of the transected tendon by being configured to inhibit an increase in a distance between first and second portions of the transected tendon.

In an application, the helical elements are configured to be screwed into respective exposed ends of the first and second portions of the transected tendon.

In an application, the helical elements are configured to not penetrate an epitenon of the tendon of the subject.

In an application, a diameter of the helical element ranges between 50% to 75% of a diameter of the tendon.

In an application, a diameter of a shaft of the helical element ranges between 3%-15% of a diameter of the tendon.

In an application, the shaft diameter is constant at at least 85% of a length of the shaft.

In an application, the helical element is formed with a textured external surface.

In an application:

each helical element has a distal end and a proximal end, the distal end of each helical element is configured to be coupled to the tissue of the subject, and the locking element includes two parts, each part of the locking element being coupled to a proximal end of a respective helical element, and the parts of the locking element being lockably couplable to each other.

In an application, one part of the locking element is shaped to define at least one slot, and the other part of the locking element is shaped to define at least one respective tab, the parts of the locking element being couplable to each other by the at least one tab being disposed in the at least one slot.

In an application, the distal end of each helical element is configured to penetrate the tissue of the subject.

In an application, the distal end of each helical element is shaped to define a cutting edge.

In an application, the distal end of each helical element is shaped to define a cutting edge that is asymmetrically tapered.

There is further provided, in accordance with an application of the present invention, a method for use with at least one tissue of a subject, the method including:

coupling a first helical element to a first portion of the tissue of the subject;

coupling a second helical element to a second portion of the tissue of the subject; and subsequently, lockably coupling the first helical element to the second helical element such that the first and second helical elements are collinear.

In an application, the method further includes, subsequent to coupling the helical elements to the portions of the tissue of the subject, and prior to coupling the first helical element to the second helical element, reducing a distance between the first and second portions of the tissue of the subject.

In an application, coupling the first helical element to the second helical element includes locking the first helical element to the second helical element.

In an application, coupling the first helical element to the second helical element does not include using suture.

In an application, coupling the first helical element to the second helical element includes inhibiting an increase in a distance between the first and second portions of the tissue.

In an application, coupling the first helical element to the second helical element includes coupling a first part of a locking element that is coupled to the first helical element, to a second part of the locking element that is coupled to the second helical element.

In an application, the locking element includes one or more tabs and one or more slots, and coupling the first part of the locking element to the second part of the locking element includes moving at least one of the tabs into at least one of the slots.

In an application, the at least one tissue includes a damaged tissue of the subject, and coupling the first and second helical elements to the first and second portions of the tissue includes coupling the first and second helical elements to first and second portions of the damaged tissue.

In an application, the method includes facilitating repair of the damaged tissue.

In an application, the first and second portions of the tissue include respective first and second portions of a transected blood vessel of the subject, and coupling the first and second helical elements includes coupling the first and second helical elements to the first and second portions of the transected blood vessel of the subject.

In an application, the first and second portions of the tissue include respective first and second portions of a transected ureter of the subject, and coupling the first and second helical elements includes coupling the first and second helical elements to the first and second portions of the transected ureter of the subject.

In an application, the first and second portions of the tissue include respective first and second portions of a transected urethra of the subject, and coupling the first and second helical elements includes coupling the first and second helical elements to the first and second portions of the transected urethra of the subject.

In an application, the first and second portions of the tissue include respective first and second portions of a transected tendon of the subject, and coupling the first and second helical elements includes coupling the first and second helical elements to the first and second portions of the transected tendon of the subject.

In an application, coupling the first and second helical elements to the first and second portions of the transected tendon includes screwing each helical element into a respective exposed end of a respective portion of the transected tendon.

In an application, coupling the first and second helical elements to the first and second portions of the transected tendon includes first and second helical elements to the first and second portions of the transected tendon without penetrating an epitenon of the tendon of the subject.

BRIEF DESCRIPTION OF THE DRAWINGS

Some embodiments of the invention are herein described, by way of example only, with reference to the accompanying drawings. With specific reference now to the drawings in detail, it is stressed that the particulars shown are by way of example and for purposes of illustrative discussion of embodiments of the invention. In this regard, the description taken with the drawings makes apparent to those skilled in the art how embodiments of the invention may be practiced.

In the drawings.

DETAILED DESCRIPTION OF EMBODIMENTS

Figure 1A:
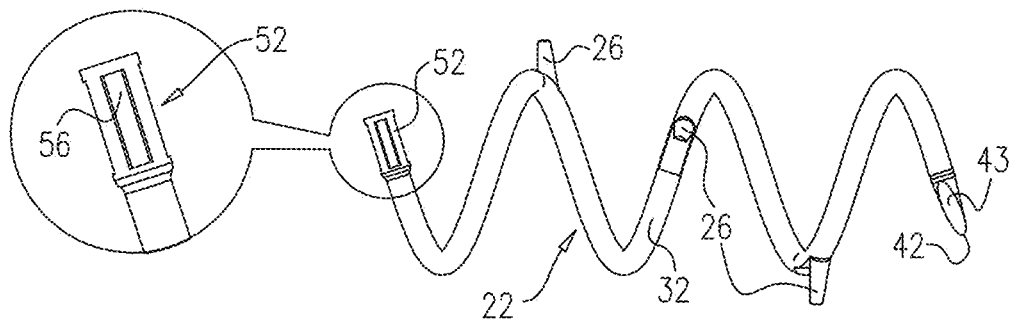
FIGS. 1A-D are schematic illustrations of a first helical element, couplable to a second helical element, for repairing a tendon, in accordance with some applications of the invention.
Figure 1B:
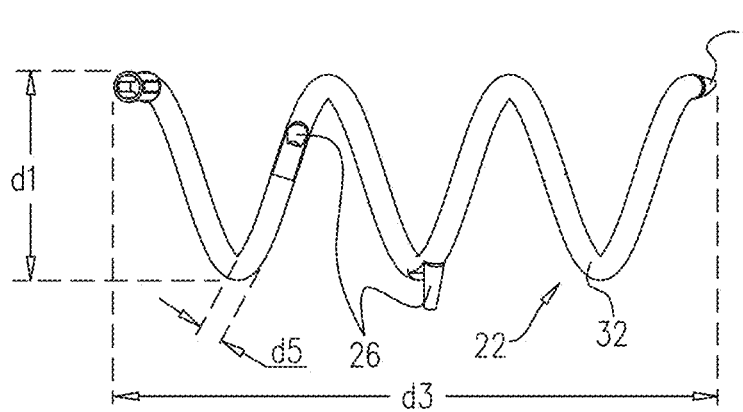
Figure 1C:
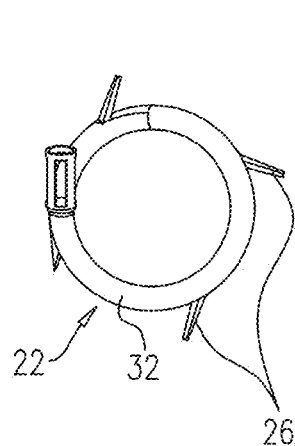
Figure 1D:
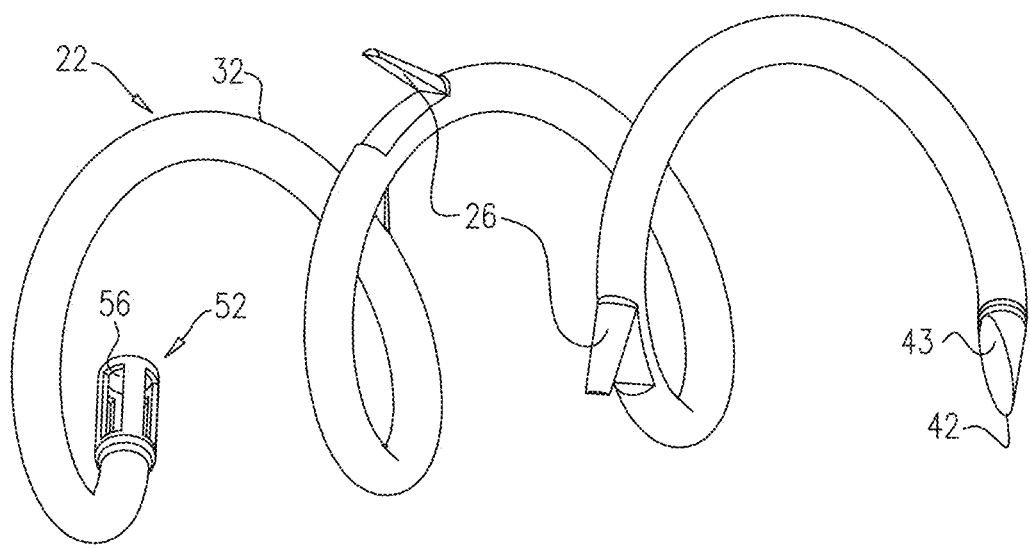
Figure 2A:
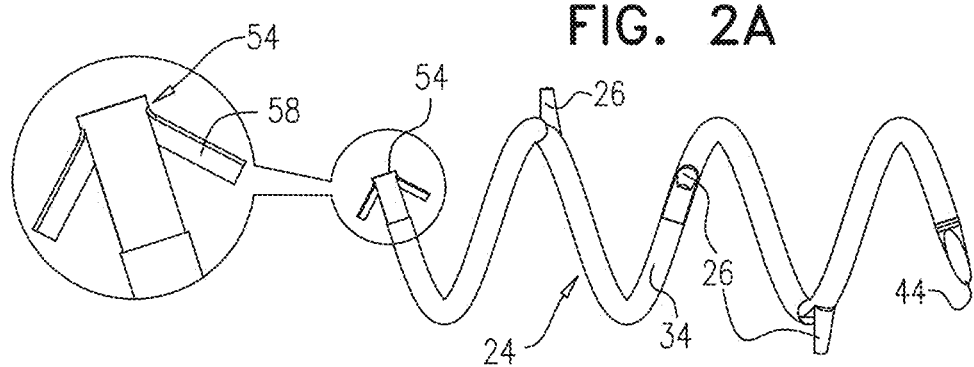
FIGS. 2A-D are schematic illustrations of the second helical element, couplable to the first helical element, for repairing the tendon, in accordance with some applications of the invention.
Figure 2B:
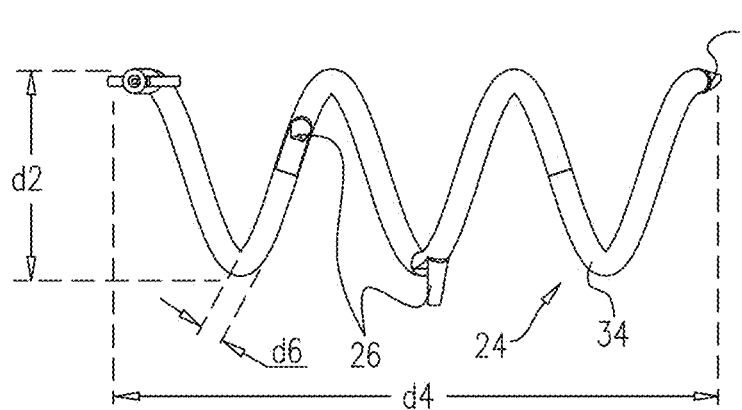
Figure 2C:
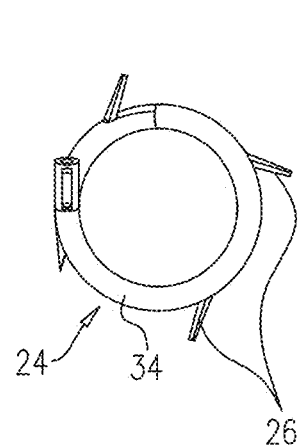
Figure 2D:
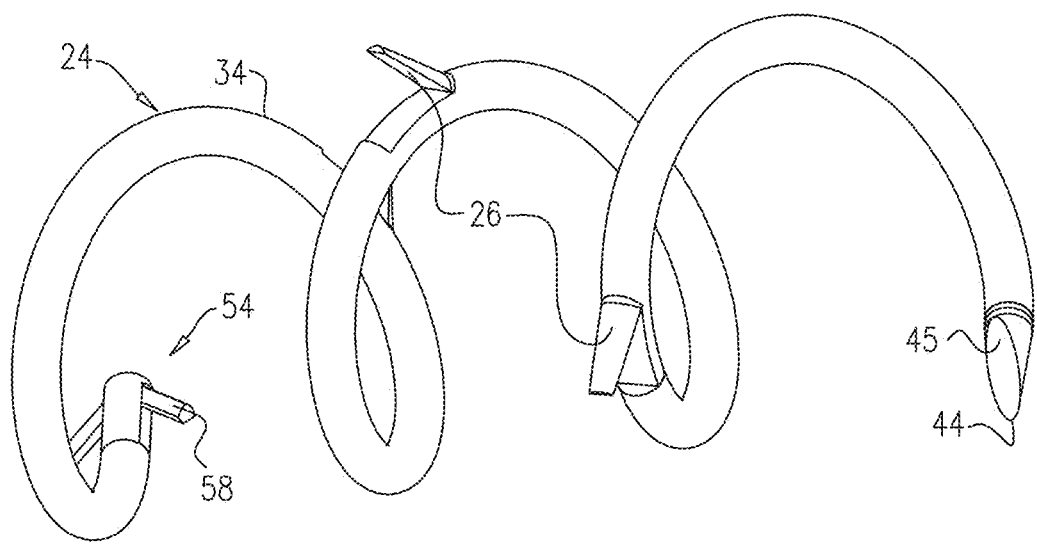

The present invention, in some embodiments thereof, relates to a tissue repair apparatus and method, and, more particularly, but not exclusively, to a tendon repair apparatus.

An aspect of some embodiments relates to a tissue repair using first and second elements, each element insertable into a tissue portion adjacent a damaged area, such as a rupture in a tendon, and a locking element configured for coupling between the first and second element to attach the tissue portions together.

In some embodiments, a shape and/or size of a repair element are selected according to a shape and/or size and/or function of a tendon intended for repair. The repair element may take various forms, for example formed as a helix, a multi-strand element having a substantially cylindrical configuration, or other configuration suitable to be positioned inside a tendon portion while least interrupting a normal function of the tendon. In some embodiments, the repair element is strong enough to withstand failure. In some embodiments, the repair element is stiff enough to withstand deformation in response to load on the tendon such as tension load. Optionally, the repair element is elastic enough to provide flexion of the tendon. In an example, a multi-strand element is selected to provide increased stiffness to a tendon in which increased stiffness is desirable, and a single strand element, such as a helical element, is selected to provide increased compliance in which increased compliance is desirable. A potential advantage of a helical element may include reducing a risk of movement such as sliding of the repair element out of the tissue, for example when compared to a straight, linear repair element which may slide out due to the substantially parallel natural arrangement of fibers in the tendon.

In some embodiments, a repair element comprises one or more projections such as teeth and/or barbs for anchoring to surrounding tissue. Optionally, the barbs are formed with rounded tips, to reduce damage to the tissue. In some embodiments, a distal end of repair element is deformable to bend in a proximal direction, anchoring against movement of the repair element in a proximal direction towards the rupture.

In some embodiments, a surface of the repair element is textured, for example comprising indentations and/or bumps and/or projections, which increase a contact area of the of the repair element with the tendon tissue. A textured surface may provide better adherence of the element to the tissue.

An aspect of some embodiments relates to a locking element for coupling two repair elements to each other, to attach between two tissue portions. In some embodiments, the locking element aligns the elements with respect to each other, bringing the proximal end faces of the tissue portions to face each other directly, such that the faces overlap. In some embodiments, a locking element is configured for setting an orientation of a first repair element with respect to a second repair element, for example by respective connector pieces configured on both proximal ends of the repair elements having matching profiles. In some embodiments, a locking element is configured to resist gap formation, for example by comprising a shape memory material which returns to its original pre-deformed configuration.

Various locking elements are described herein, such as a locking element in the form of a slot and respective tab, a locking element comprising a "snap-on" mechanism, a locking element comprising male and female connectors comprising a projection and matching recess respectively, a locking element configured at a proximal end of a first repair element, formed with a recess shaped and sized for receiving a proximal end of a second repair element, and others. In some embodiments, the locking element is crimped to fasten the proximal ends of the repair elements together. In some embodiments, a connector of the locking element projects externally to a proximal end of a first tendon portion, and the respective connector is embedded within a proximal end of a second tendon portion, to overlap each other when connected.

In some embodiments the locking element comprises two connectors. Alternatively, the locking element comprises one connector suitable for engaging a proximal end of the second repair element.

In some embodiments, the locking element is elastic enough to enable bending of the flexion of the repaired tendon.

In some embodiments, the locking element is configured to provide axial rotation and/or articulation of the tendon portions with respect to each other. A potential advantage of a locking element providing a certain freedom of movement, such as axial rotation, may include increasing a healing rate of the repaired tendon.

In some embodiments, the locking element is sized so that it does not extend beyond a periphery of the repaired tendon. Optionally, a diameter of a connector is smaller than a diameter of the tendon, for example 20%, 40%, 60%, 80%, 90%, or intermediate, larger or smaller percentages smaller. In some embodiments, a cross section area of the connector is small enough so that it does not add bulkiness to the repaired tendon.

In some embodiments, the locking element, comprising one or two connectors, is positioned axially with respect to the tendon. A potential advantage of an axial positioning may include facilitating the connection between the repair elements. Alternatively, the locking element is positioned at a non axial position with respect to the tendon, for example positioned at a continuation of a helical repair element, thereby positioned at a radially outward distance from the longitudinal axis of the tendon. A potential advantage of a non-axial position may include a better resistance to load such as tension load acting on the tendon, as the connector is positioned offset from an axis on which the strongest effect of the load exists.

In some embodiments, a length of the locking element ranges between, for example, 5-20%, 10-30%, 2-7% or intermediate, larger or smaller ranges of a length of each of the repair elements.

An aspect of some embodiments relates to treating damaged tissue by coupling between tissue portions using a repair apparatus. In some embodiments, a repair element is introduced into a tissue portion from an end face of the tissue portion adjacent the rupture, and advanced in a distal direction within the tissue.

In some embodiments, a delivery device is used for introducing the repair element into the tissue. Optionally, the delivery device is pre-loaded with the repair element, and is configured to dispose the repair element within the tissue. In some embodiments, the delivery device comprises a cutting edge for forming a path within the tissue, into which the repair element inserted. In some embodiments, the repair element is advanced within the delivery device by a "push-click" mechanism, involving pressing a knob multiple times to incrementally advance the repair element into the tissue. Additionally or alternatively, a needle is used with the repair element. Optionally, the repair element is delivered over the needle into the tissue, and once the repair element is positioned in place, the needle is removed, such as by pulling it in a proximal direction.

In some embodiments, at least the proximal ends of the tissue portions intended to be coupled to each other are held in proximity to each other, for example by a gripper device. Optionally, the gripper device comprises two portions that are assembled together to form a sleeve-like configuration, for example having a first portion with a smaller diameter fitting within a portion of larger diameter to bring the tissue ends together. In some embodiments the gripping device holds the tissue portions at a distance from their proximal ends, to enable connecting the ends together. In some embodiments, the gripping device comprises one more windows providing access to the connection site.

In some embodiments, a coupling established between the tissue portions by the locking element is assessed, for example by verifying linear movement of the tendon inside the tendon sheath.

A "proximal end" of a tissue as referred to herein may include an end portion of a tissue portion which is closest to the damaged area, for example an end of a tendon portion adjacent a gap formed between two opposing tendon portions, which previously formed a single tendon together.

A "proximal end" of a tissue repair element as referred to herein may include an end portion of a repair element which is closest to the damaged area, for example an end of a repair element adjacent a gap formed between two tendon portions.

A "distal end" of a repair element as referred to herein may include an end portion of a repair element which engages the tissue, for example in some cases configured to be advanced distally and away from the damaged area in tissue such as a tendon portion.

An Exemplary Method for Implanting a Tissue Repair Apparatus

Figure 5:
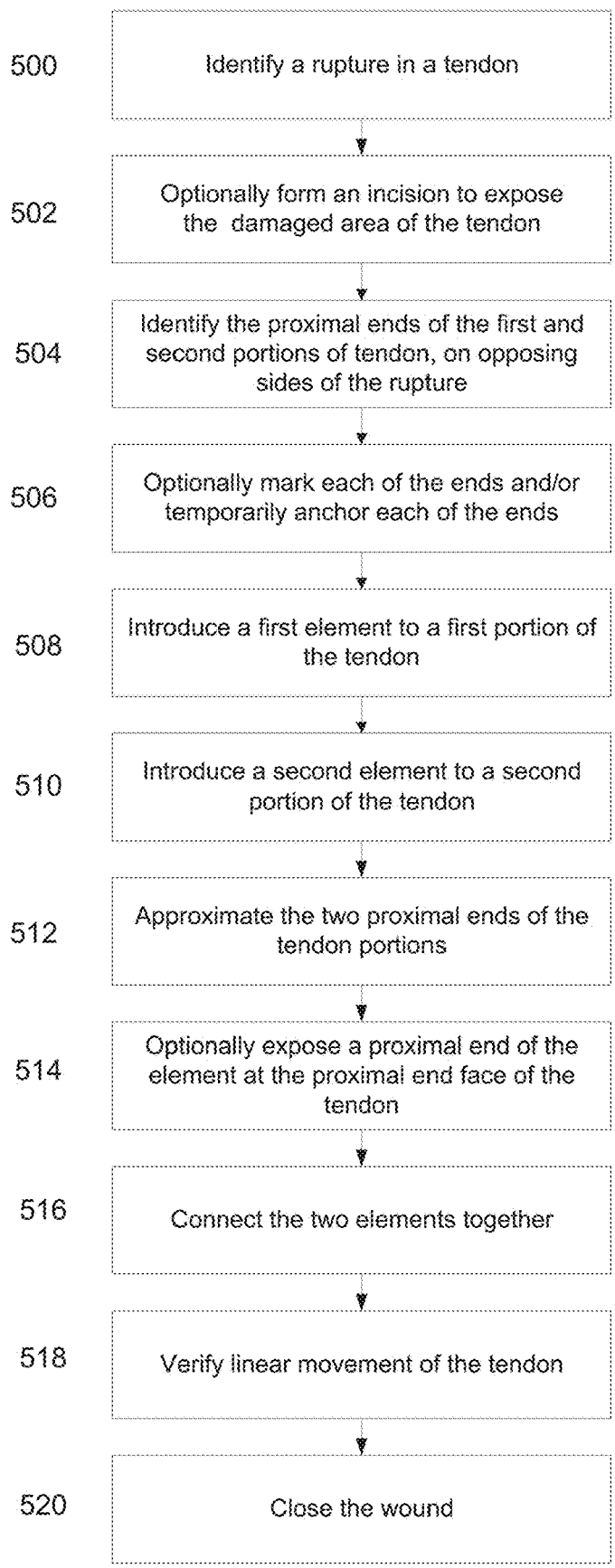
FIG. 5 is a flowchart of a method for implanting a tissue repair apparatus, according to some embodiments of the invention.

Reference is made to the flowchart of FIG. 5, describing an exemplary method for implanting a tissue repair apparatus, according to some embodiments of the invention. The method described herein refers to repair of a damaged tendon, but it is noted that the method and/or apparatus may be used with other tissue types.

In some embodiments, the tendon repair apparatus is implanted to attach between portions of a damaged tendon. In some cases, the tendon is damaged as a result of, for example, a tear, a cut, a blow, wear, inflammation, arthritis, sports injury and/or other causes of damage. In some cases, the tendon portions detach from each other. In some cases, a gap is formed between the separated ends of the tendon portions. Alternatively, the portions remain partially attached to each other, for example by one or more collagen fibers of the tendon which have not been damaged. In some cases, a tear is formed straight across the tendon. In some cases, a tear is formed at an angle.

In some embodiments, a rupture is identified in the tendon (500). In some cases, the rupture is visible, for example if it was caused by a cut. Additionally or alternatively, imaging is used to identify the rupture. Additionally or alternatively, the physician palpates the tendon to locate the damaged area.

Optionally, an incision is formed in the tissue to provide access to the damaged tendon (502). In some embodiments, the proximal ends of the first and second tendon portions are identified. In some cases, the proximal ends may be distanced apart from each other. Optionally, the physician reaches to clamp the ends of the tendon portions, for example by using tweezers or any other tool suitable for clamping the tendon. In some embodiments, the physician marks the ends of the tendon portions and/or temporarily anchors them in place (506), for example by pinning a needle through. In some embodiments, a segment of a tendon portion is removed, for example to provide access for insertion of the repair element and/or to otherwise facilitate the connection.

In some embodiments, the physician is provided with a kit including tendon repair elements of various sizes and/or shapes, and a suitable element is selected. Optionally, the element is selected according to a diameter and/or length and/or condition of the tendon portion to be treated. In some embodiments, the kit includes a delivery device. Optionally, the delivery device is pre-loaded with a repair element. In some embodiments, the delivery device is disposable.

In some embodiments, a repair element is selected to have a diameter of, for example, between 20%-75%, 45-65%, 30%-55%, 30%-80% or intermediate, larger or smaller percentages of a diameter of a tendon portion in which it is intended to fit. In an example, a repair element in the form of a helix is selected to have a diameter which is ⅔ of a diameter of a tendon cross section diameter. Optionally, a diameter of the shaft forming the helix ranges between, for example, 10%-40%, 5%-20%, 15%-45% or intermediate, larger or smaller percentages of a diameter of the helix.

In some embodiments, the shaft comprises a circular profile, a triangular profile, or other profile. Optionally, the profile is an a-traumatic profile, such as to reduce damage to the tissue upon insertion.

In some embodiments, a diameter of a shaft or wire forming the repair element is selected to be, on one hand, thick enough to withstand load acting on the tendon, and, on the other hand, thin enough so as to least affect the flexibility of the tendon.

In an example, for a tendon having a diameter of 3 mm, a helical repair element having a diameter of 2 mm and a wire diameter of 0.4 mm would be used.

In some embodiments, a first element of the tendon repair apparatus is introduced to a first portion of the tendon (508). Optionally, the element is introduced via a delivery device, for example as further described herein. In some embodiments, the element is inserted into the tendon portion from the proximal end. Optionally, the element is pushed in a distal direction within the tendon portion. Optionally, the element is rotated axially to enter the tendon. In some embodiments, a proximal end of the element is formed with one or more cutting edges, effective to form a path through the tendon as the element is advanced in a distal direction.

In some embodiments, an extent to which the element is inserted in a distal direction into the tendon portion rages between, for example, 5% to 70% of the length of the tendon portion.

In some embodiments, a second tendon repair element, configured to engage the first tendon repair element, is introduced into the second tendon portion (510).

In some cases, if the proximal ends of the tendon portions are located a distance from each other, the ends are approximated towards each other (512), for example by the physician and/or with the aid of a delivery device.

When the proximal ends of the tendon portions are close enough to be attached to each other, a proximal end of the element is optionally exposed to protrude externally from a proximal face of the tendon. Optionally, the proximal end of the element comprises a connector piece for engaging the respective second element positioned at the second tendon portion.

In some embodiments, the proximal ends of the two elements are connected to each other (516). Optionally, depending on the type of the connectors used, connecting involves threading, rotating, snapping, clicking, pushing and/or crimping the locking elements at the proximal ends of the tendon repair elements.

In some embodiments, after the attachment between the tendon portions is established, movement of the tendon is verified (518). Optionally, linear movement of the tendon such as within the tendon sheath surrounding the tendon is verified. In some embodiments, verifying the movement comprises flexing or extending a bone joint to which the tendon is attached, for example by bending a finger in the case of a repaired flexor tendon. In some embodiments, the physician ensures that there is no substantial bulkiness in the re-attached tendon. Optionally, if the attachment is found to be impaired, for example if it restricts desired movement of the tendon, one or more of steps 508-518 may be repeated.

It is noted that in some embodiments, steps 510-514 may be performed in a different order.

After completing the attachment procedure of the two tendon portions, the wound is closed (520), for example by stitching.

In some cases, if multiple sites of injury exist in the tendon, the procedure is repeated at the various sites. In some cases, it may be decided to use more than one repair element for a tendon portion, for example if the tendon is large in diameter and/or if additional anchoring strength is required. Optionally, multiple repair elements occupy a larger cross sectional area of the tendon, and may provide a better hold of the tendon portion.

Tissue Repair Elements Configured as Helical Elements

Reference is made to FIGS. 1A-D and 2A-D, which are schematic illustrations of tissue repair apparatus 20, comprising a first repair element in the form of a helical element 22 and a second repair element in the form of helical element 24 that is couplable to the first helical element, in accordance with some applications of the invention. Apparatus 20 is not labeled in FIG. 1A-D or 2A-D because, in these figures, helical elements 22 and 24 are not shown together. Apparatus 20 is labeled in FIGS. 3C and 4A-B. FIGS. 1A-D show helical element 22, and FIGS. 2A-D show helical element 24.

Helical elements 22 and 24 are configured to be coupled to respective portions of tissue of a subject, and to be lockably coupled to each other. Typically, apparatus 20 is configured such that helical elements 22 and 24 are couplable to each other after the helical elements are coupled to the respective portions of tissue. Apparatus 20 is thereby configured to hold together the respective portions of tissue of the subject (i.e., to inhibit an increase in a distance between the portions of tissue). Apparatus 20 is typically configured, and used, to facilitate repair of a transected (e.g., torn or cut) tendon of a subject, as described hereinbelow, e.g., with reference to FIGS. 3A-C. Alternatively, apparatus 20 may be configured to facilitate repair of other tissues (e.g., other elongate tissues, such as a blood vessel, ureter, or urethra of the subject).

Helical elements 22 and 24 each comprise a shaft 32 and 34, respectively, which are shaped to define respective helices. Typically, each helix has a transverse cross-sectional diameter of more than 0.2 mm and/or less than 10 mm (e.g., 0.5 mm-5 mm, such as 1 mm-5 mm), and a length of more than 0.5 cm and/or less than 3 cm (e.g., 0.5 cm-2 cm, such as 0.5 cm-1.5 cm). That is, helical elements 22 and 24 typically have (1) respective diameters d1 and d2 of more than 0.2 mm and/or less than 10 mm, and (2) respective lengths d3 and d4 of more than 0.5 cm and/or less than 3 cm.

Typically, the shafts comprise a metal such as, but not limited to, stainless steel, titanium, nickel titanium (Nitinol), nickel cobalt, and/or cobalt chrome. For some applications, the shafts comprise a polymer and/or a resin. Shafts 32 and 34 have respective cross-sectional diameters (e.g., bores) d5 and d6, which may be dimensioned according to specific applications, e.g., according to the tissue being repaired. Similarly, the pitch of the helix of the shafts may be configured according to specific applications.

Shafts 32 and 34 each have a distal end 42 and 44, respectively, configured to be coupled to the tissue (e.g., the tendon) of the subject, typically by being configured to penetrate, and to be screwed into, the tissue. For example, distal ends 42 and 44 may be shaped to define respective cutting edges 43 and 45. Typically, the cutting edges are asymmetrically tapered (e.g., generally chisel-shaped, such as in an atraumatic needle, as is known in the art). For example, the cutting edge may be formed by cutting and/or grinding the shaft from one side of the shaft only. For some applications, and as shown, the taper of the cutting edge of each helical element is on the inside of the helix formed by the shaft, such that the distal-most point of the cutting edge (e.g., the distal end of the shaft) is on the outside of the helix. Alternatively, the taper may be on the outside of the helix.

In some embodiments, distal ends 42 and 44 are configured for penetrating and/or passing through fibers and/or fiber bundles within the tendon.

Typically, the helix defined by shaft 32 of element 22, and the helix defined by shaft 34 of element 24, have the same handedness. That is, helical element 22 and helical element 24 typically have the same handedness.

Typically, helical elements 22 and 24 comprise, or are shaped to define, one or more projections 26 (e.g., flanges), that are configured to generally allow the helical element to enter the tissue (e.g., when it is screwed into the tissue, as described hereinbelow, such as with reference to FIGS. 3A-C), but to inhibit movement of the helical element in the reverse direction (e.g., to inhibit inadvertent movement of the helical element out of the tissue). Typically, projections 26 are configured to flatten against the shaft of the helical element when the helical element is moved (e.g., screwed) into the tissue. For some applications, the shaft and projections comprise a continuous piece of material (e.g., projections 26 are formed, such as cut and/or splintered, from the shaft). For some applications, the projections comprise discrete pieces of material and are coupled to the shaft.

In some embodiments, projections 26 are elastic. In some embodiments, a length of projections 26 ranges between, for example, 5-60%, 10-40%, 1-10% or intermediate, larger or smaller ranges of a diameter of the shaft.

Typically, apparatus 20 further comprises a locking element 50, comprising a first part 52, coupled to helical element 22, and a second part 54, coupled to helical element 24. Locking element 50 is not labeled in FIG. 1A-D or 2A-D because, in these figures, parts 52 and 54 are not shown together. Locking element 50 is labeled in FIGS. 3C and 4A-B. FIGS. 1A-D show part 52, and FIGS. 2A-D show part 54. Parts 52 and 54 are lockably couplable to each other, and helical elements 22 and 24 are lockably couplable to each other by parts 52 and 54 of locking element 50 being coupled to the helical elements, and being lockably couplable to each other.

For some applications, parts 52 and 54 are generally irreversibly couplable to each other. For some applications, parts 52 and 54 are reversibly couplable to each other.

For some applications, one of the parts of locking element 50 is shaped to define one or more slots 56, and the other part of the locking element comprises one or more tabs 58, each tab being disposable in a respective slot. FIGS. 1A-4B show part 52 being shaped to define slots 56, and part 54 comprising tabs 58. For some applications, both parts of the locking element are shaped to define one or more slots 56 and/or comprise one or more tabs 58.

Typically, tabs 58 are configured to (1) generally allow movement thereof into slots 56, and (2) generally inhibit movement thereof out of the slots. For example, tabs 58 may be (1) disposed circumferentially around part 54, (2) configured to move radially inward when pushed into the part 52, and (3) configured to move radially outward when the tabs reach slots 56. FIGS. 1A-4B show slots 56 exposed on the outer surface of part 52, and, when the two parts of locking element 50 are coupled to each other, tabs 58 protruding through the slots and exposed from the outer surface of part 52. For some applications, the outer surface of locking element 50 (e.g., the outer surface of part 52 thereof) is smooth and/or flush with the surface of the shafts of the helical elements. For example, slots 56 may be not exposed on the outer surface of part 52, and tabs 58 may protrude into, but not through, the slots.

Figure 3A:
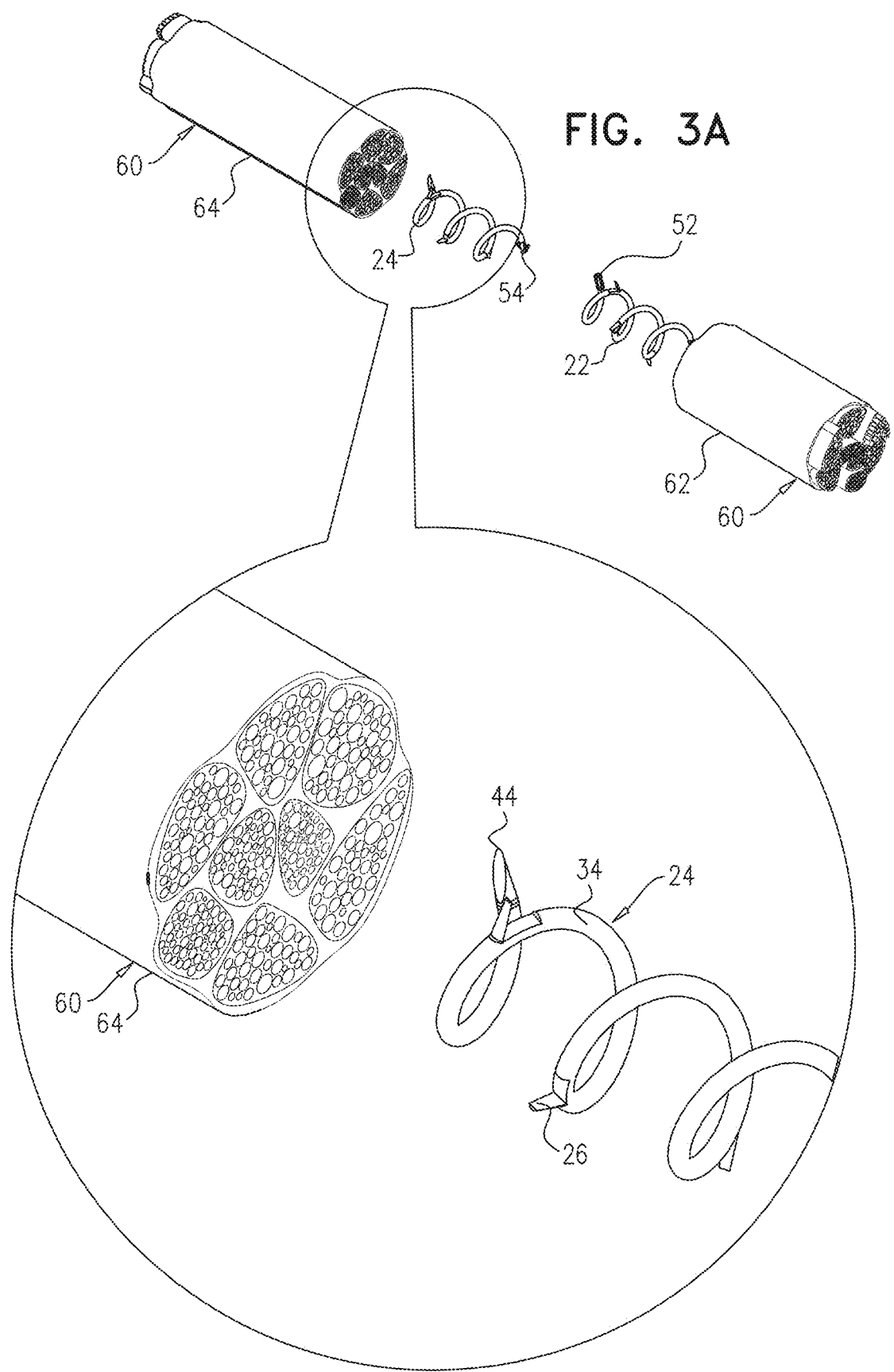
FIGS. 3A-C are schematic illustrations of apparatus, comprising the first and second helical elements, being used to repair the tendon, in accordance with some applications of the invention.
Figure 3B:
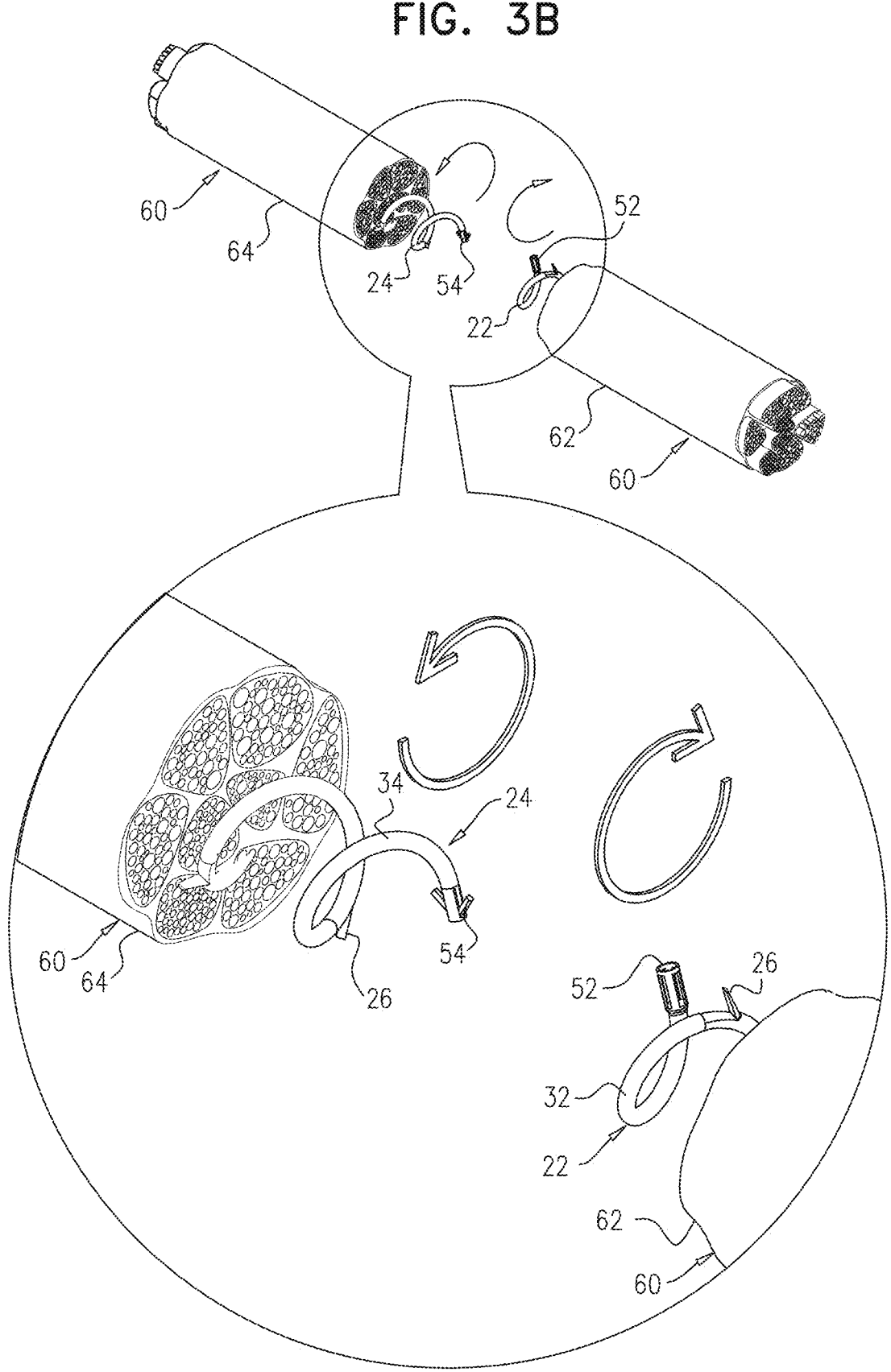
Figure 3C:
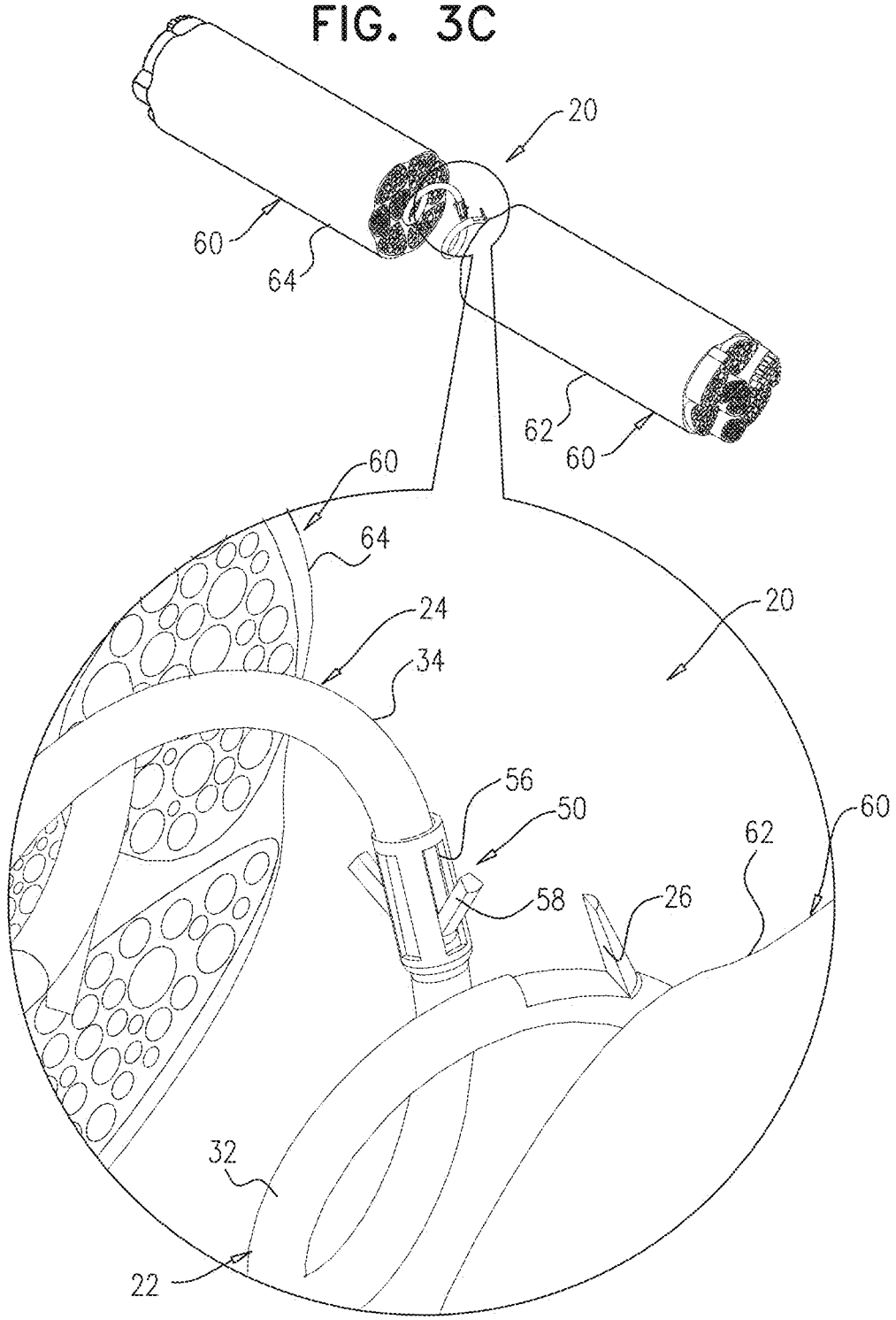

Reference is made to FIGS. 3A-C, which are schematic illustrations of apparatus 20, being used to repair a tendon 60 that has been previously transected into a first portion 62 and a second portion 64 (e.g., in an injury), each portion having an exposed end at the point of transaction. FIG. 3A shows helical elements 22 and 24 positioned for coupling to portions 62 and 64 of the tendon, respectively.

FIG. 3B shows helical elements 22 and 24 being coupled to portions 62 and 64 of the tendon, respectively, by being screwed into the portions of the tendon. The cutting edge at the distal end of each helical element facilitates penetration of the tissue (i.e., the tendon). Typically, the helical elements are screwed into the portions of the tendon via the exposed ends of the portions of the tendon. Typically, the helical elements are screwed into the portions such that the helical elements do not exit the lateral surface of the tendon and/or do not penetrate the surrounding structure of the tendon (e.g., fibrous or synovial sheaths, epitenon, paratenon, and/or tendon bursae). It is hypothesized that such positioning facilitates normal movement (e.g., sliding) of the tendon with respect to the surrounding structure.

FIG. 3C shows helical elements 62 and 64 of apparatus 20 having been lockably coupled to each other, subsequent to their coupling to (e.g., screwing into) the respective portions of tendon 60. Typically, and as shown in FIG. 3C, the helical elements are coupled to each other such that they are disposed collinearly with each other. For some applications, and as shown in FIG. 3C, the helical elements are configured such that, when the helical elements are coupled to each other, they form a continuous helix.

For applications in which apparatus 20 comprises locking element 50, helical elements 22 and 24 are lockably couplable to each other by parts 52 and 54 of locking element 50 being coupled to the helical elements, and lockably couplable to each other. As shown in FIG. 3C, for applications in which one of the parts of locking element 50 is shaped to define one or more slots 56, and the other part of the locking element comprises one or more tabs 58, when the tabs reach respective slots, the tabs move radially outward into the slots, thereby lockably coupling the helical elements to each other.

It is to be noted that locking element 50 typically does not comprise suture (e.g., thread, wire, or similar), and thereby repair of tendon 60 using apparatus 20 is typically performed without the use of suture (except for the closure of a surgical access incision). Alternatively, the parts of locking element 50 may be configured to be coupled to each other using suture. Additionally, the parts may be configured to be brought together using the suture, e.g., by slidably coupling the suture to at least one of the parts and tightening the suture.

Figure 4A:
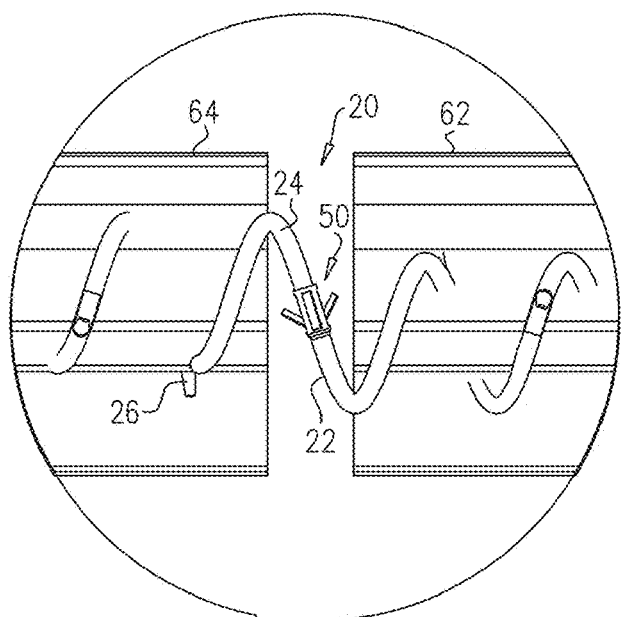
FIGS. 4A-B are schematic illustrations of the apparatus, comprising the first and second helical elements, having been used to repair the tendon, in accordance with some applications of the invention.
Figure 4A:
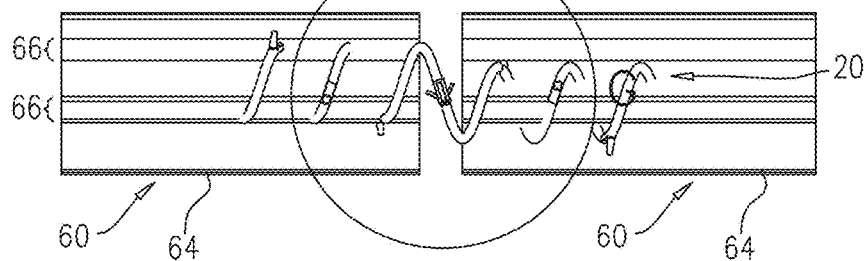
Figure 4B:
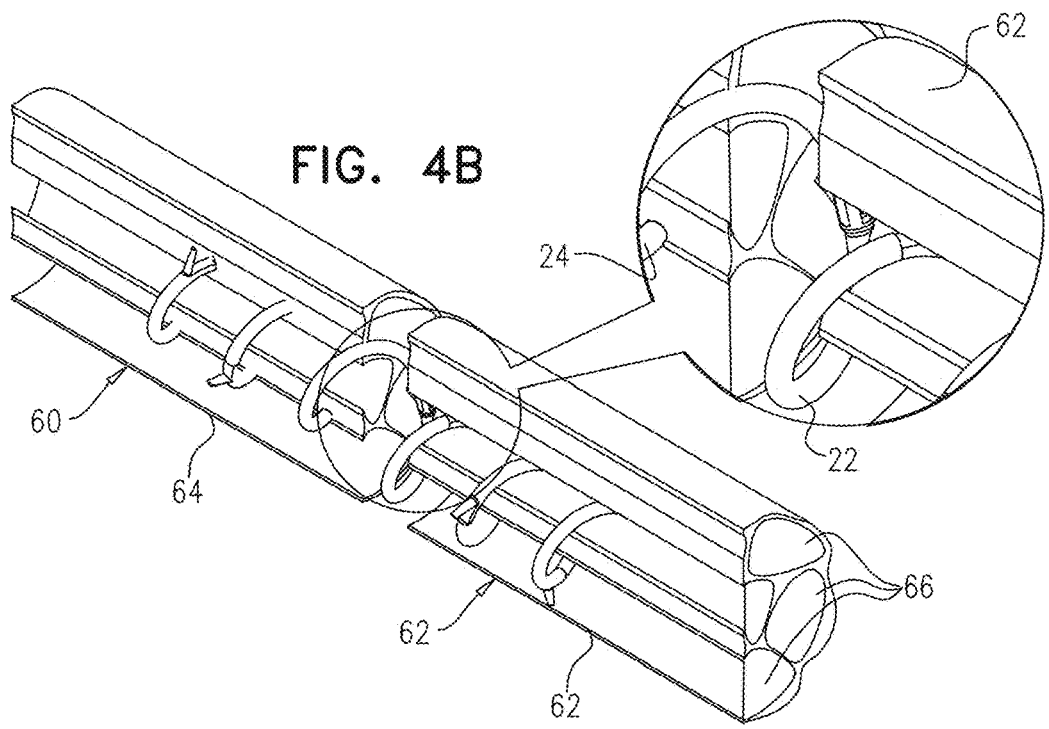

Reference is made to FIGS. 4A-B, which are schematic illustrations of apparatus 20, coupling the two portions of transected tendon 60 to each other, in accordance with some applications of the invention. FIG. 4A is a two-dimensional cutaway, and FIG. 4B is a three-dimensional cutaway. As described hereinabove, helical elements 22 and 24 are typically screwed into the portions of the tendon via the exposed ends of the portions. Also as described hereinabove, the helical elements typically do not exit the lateral surface of the tendon.

As shown in FIGS. 4A-B, each helical element is typically screwed into a respective portion of the tendon such that the shaft of the helical element is coiled around one or more fiber bundles (e.g., fascicles and subfascicles), and/or penetrates one or more of the fiber bundles. It is hypothesized that this arrangement of the helical elements within the tendon increases contact between the helical elements and structures of the tendon, thereby increasing the strength of the coupling of the helical elements to the tendon portions and, thereby, increasing the strength of the coupling of the tendon portions to each other. It is further hypothesized that this increased strength of coupling reduces slipping of the helical elements within the tendon portions, and thereby inhibits any increase in a distance between the tendon portions following coupling of the two helical elements to each other.

Reference is again made to FIGS. 3C-4B. For clarity, FIGS. 3C-4B show a gap between portions 62 and 64 of tendon 60, and show parts 52 and 54 of locking element 50 protruding from the exposed ends of the tendon. However, typically, the helical elements are screwed into the tendon such that little or none of the helical elements and/or the parts of the locking element protrude from the exposed ends. Typically, the tendon (e.g., the portions thereof) are sufficiently soft and/or pliable that the exposed ends may be temporarily squashed together during the coupling of the two parts of locking element 50, thereby facilitating this coupling even when little or none of the parts of the locking element are exposed from the exposed ends of the tendon.

FIGS. 3A-4B show apparatus 20 being used to couple two portions of a tendon, so as to repair the tendon. However, it is to be noted that the scope of the present invention includes the use of apparatus 20 to couple other tissues. In particular, the scope of the present invention includes the use of apparatus 20 to repair other transected elongate and/or tubular tissues, such as a transected blood vessel, ureter, or urethra.

Tissue Repair Elements Configured as Multiple-Strand Elements

Figure 6A:
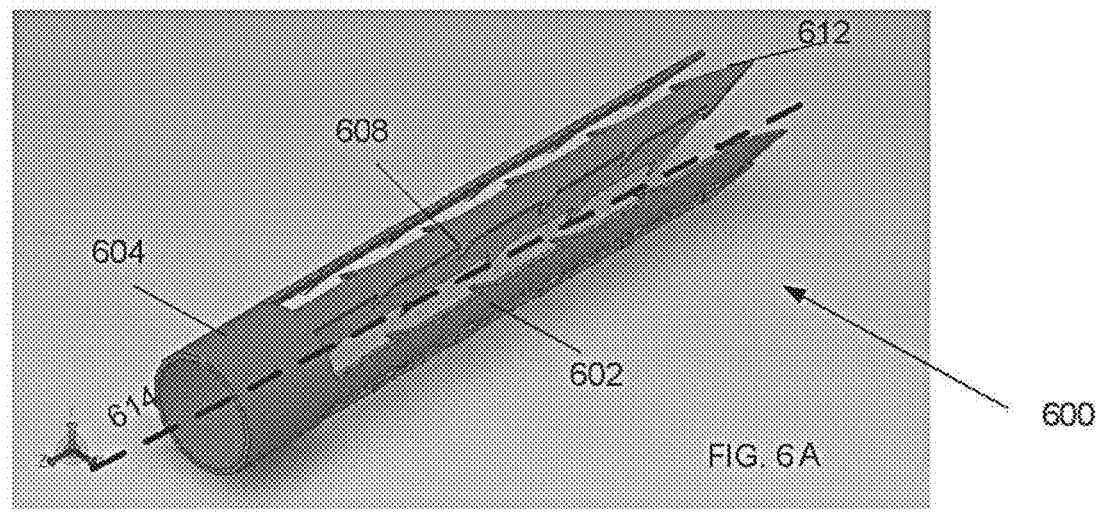
FIGS. 6A-D illustrate a tissue repair element comprising multiple strands, according to some embodiment of the invention.
Figure 6B:
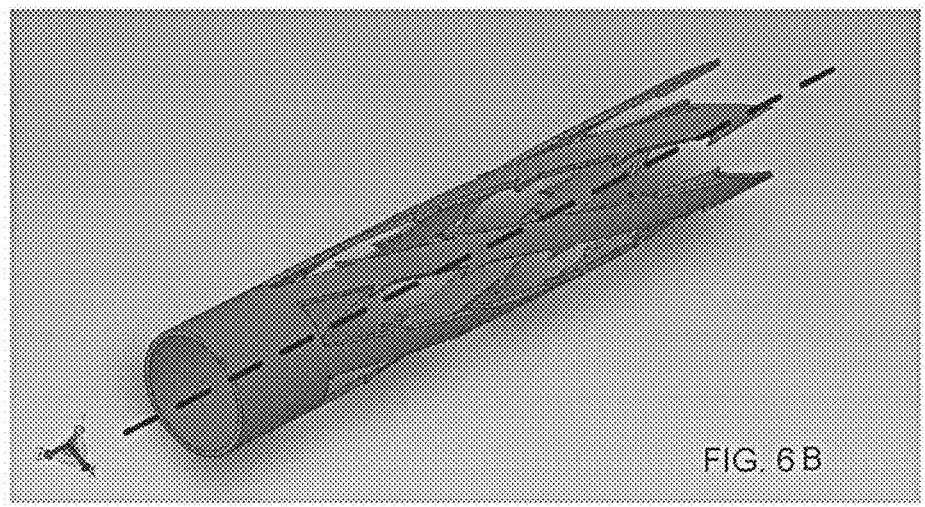
Figure 6C:
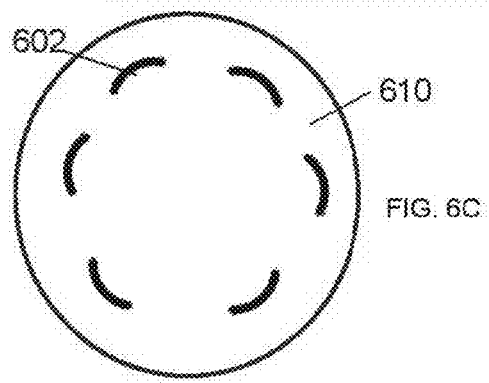

Reference is now made to FIG. 6A-C, showing an exemplary configuration of a tissue repair element comprising multiple strands, according to some embodiments of the invention.

In some embodiments, element 600 comprises a plurality of strands 602, such as cables or wires, arranged in a cylindrical configuration.

In some embodiments, strands 602 are attached at their proximal ends to a cylindrical shaft portion 604. Optionally, cylindrical shaft portion 604 is shaped and/or sized for receiving a respective proximal end of a second, corresponding element which is inserted into the second tissue portion, for example by being formed with a larger diameter than the respective proximal end of the second element. Additionally or alternatively, cylindrical shaft portion 604 is configured to receive a locking element.

In some embodiments, strands 602 are aligned in parallel with respect to each other and with respect to a longitudinal axis 614 of the element, for example as shown in FIG. 6A. Alternatively, for example as shown in FIG. 6B, strands 602 are wound around central axis 614. A potential advantage of winding strands may include obtaining a better grip on the tissue, such as tendon tissue, for example with respect to a repair element formed with parallel strands, as the tendon is comprised of substantially parallel collagen fibers, and parallel strands of the repair element may move linearly and/or slip away from the tendon fibers.

In some embodiments, strands 602 comprise one or more projections, such as barbs 608. Optionally, barbs 608 taper in the proximal direction, enabling movement of the element in the distal direction within the tissue, but limiting movement of the element in the proximal direction by penetrating the tissue and anchoring element 600 in place. In some embodiments, barbs 608 comprise a rounded tip, to reduce damage to the tissue, for example when strands 602 are pulled back in a proximal direction.

Figure 6D:
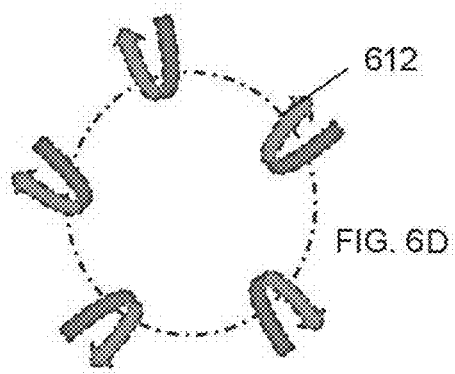

In some embodiments, at least the distal ends 612 of strands 602 are elastic. Optionally, strands 602 are formed of a shape memory material, such as nitinol. In some embodiments, for example as shown in FIG. 6D, distal ends 612 are bendable in a radially outward and proximal direction. When element 600 is advanced into the tissue and positioned in place, distal ends 612 may bend in the proximal direction, for example in a 130-180 degree angle, penetrating the surrounding tissue to anchor element 600 in place. In some embodiments, for example when element 600 is delivered with the aid of a delivery device, distal ends 612 bounce back in the proximal direction upon being released from the delivery device.

In some embodiments, for example as shown in FIG. 6C, strands 602 occupy, for example, 5%-20%, 10%-30%, 7%-15% or intermediate, larger or smaller percentages of a cross-sectional area 610 of a tissue such as a tendon portion. Optionally, the strands are distributed circumferentially.

A potential advantage of a repair element comprising a plurality of strands may include a better distribution of load, for example as compared to single strand element. The multiple-stranded element may obtain a more secured hold of the tendon portion. Another potential advantage of a plurality of strands may include increasing a stiffness of the tendon, thereby providing increased deformation resistance in response to load applied on the tendon.

In some embodiments, strands 602 are formed with recesses, such as recesses arranged along a length of a strand. A potential advantage of recesses may include increased axial flexibility of the repair element.

Insertion of a Tissue Repair Element with the Aid of a Needle

Figures 7A, 7B, 7C:
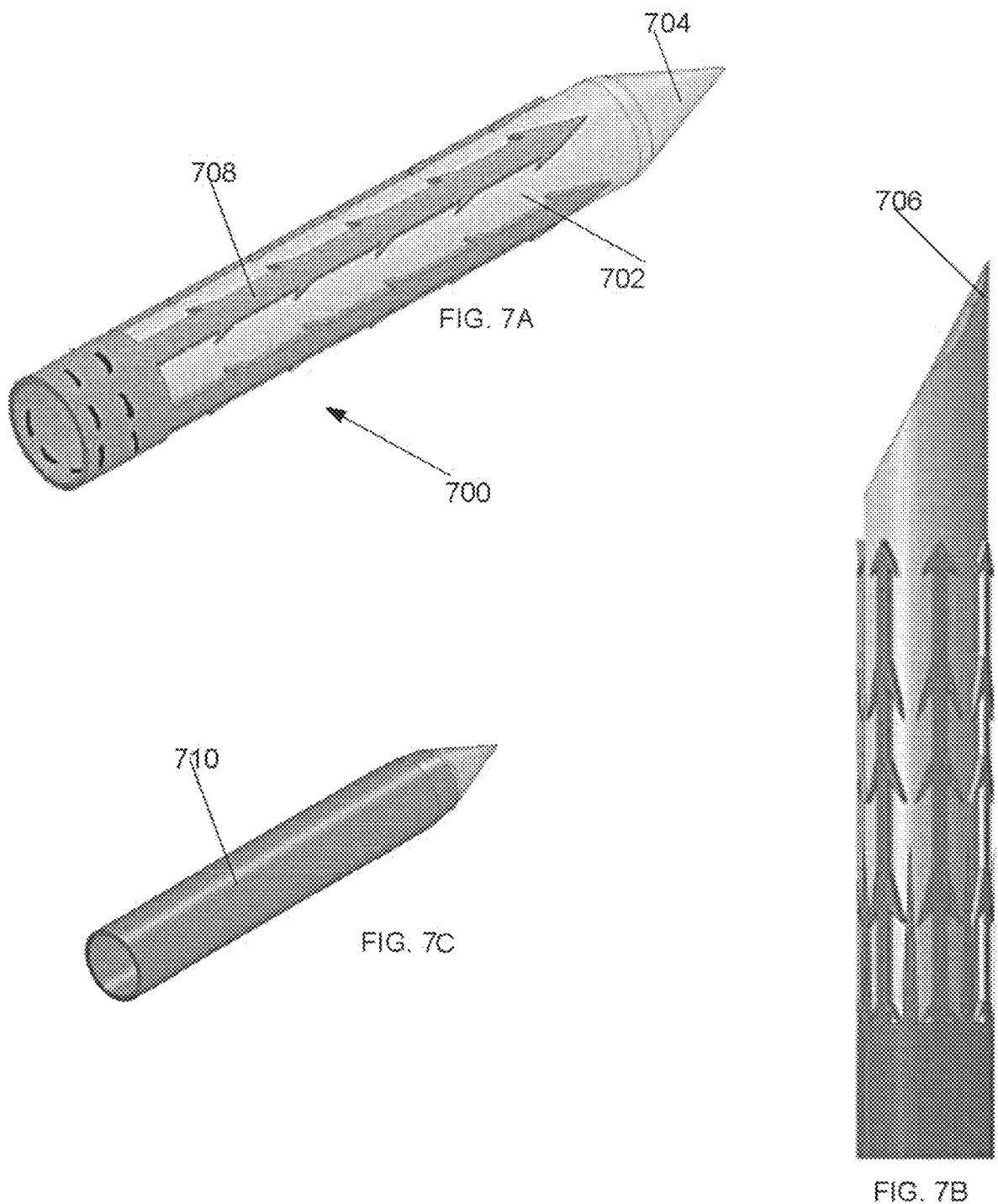
FIGS. 7A-C illustrate a tendon repair element introduced to the tendon over a needle, according to some embodiments of the invention.

FIG. 7A-B show an exemplary repair element 700 which is insertable into tissue such as a tendon over a needle 702. In some embodiments, repair element 700 is threaded over needle 702, and is advanced into the tendon portion over the needle. In some embodiments, for example as shown in FIG. 7A, needle 702 comprises a conical distal tip 704. Alternatively, for example as shown in FIG. 7B, needle 702 comprises a tapered cutting edge 706. Optionally, cutting edge 706 has an a-traumatic profile.

In some embodiment, needle 702 is rotated when advanced into the tendon portion. Optionally, element 700 is coupled to the needle in a way that its strands 708 are axially rotated when the needle is rotated, transforming the element to a configuration for example as shown in FIG. 6B.

In some embodiments, needle 702 is removed once element 700 is positioned in place, for example by pulling the needle in the proximal direction.

In some embodiment, for example as shown in FIG. 7C, needle 702 is coated by a thin coating 710, for example a thin layer of silicon, Teflon, hydroxyapatite, and/or porous coating such as porous foam metal. In some embodiments, repair element 700 is coated by a thin coating. In some embodiments, coating 710 covers only some portions of the needle and/or repair element, for example arranged in axially extending strips, axial segments, covering only the tip portion, or other configurations. Some potential advantages of a coating may include a smoother insertion process, reducing damage to the tissue. By reducing damage to the tissue, the repair element may obtain a better grip on the tissue, before, during and/or after healing of the tissue.

In some embodiments, repair element 700 is coated and/or eluted with drugs, growth factors, tissue adhesive materials, and/or other bio-active materials, such as materials suitable for increasing a healing rate and/or strengthening the repaired tissue.

In some embodiments, repair element 700 can be coated by a layer of stem cells. A potential advantage of a stem cell coating may include inducing tissue growth.

A Tissue Repair Element with Surface Modifications

Figure 8A:
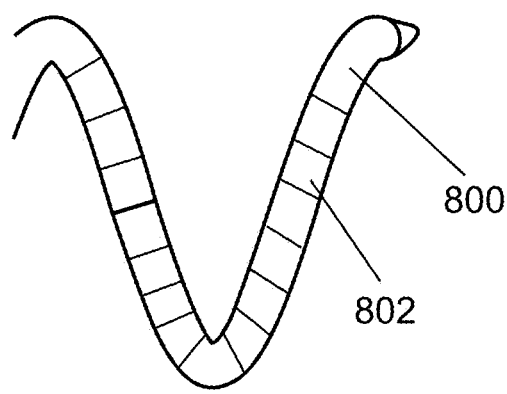
FIGS. 8A-B show a tissue repair element formed with surface modifications, according to some embodiments of the invention.
Figure 8B:
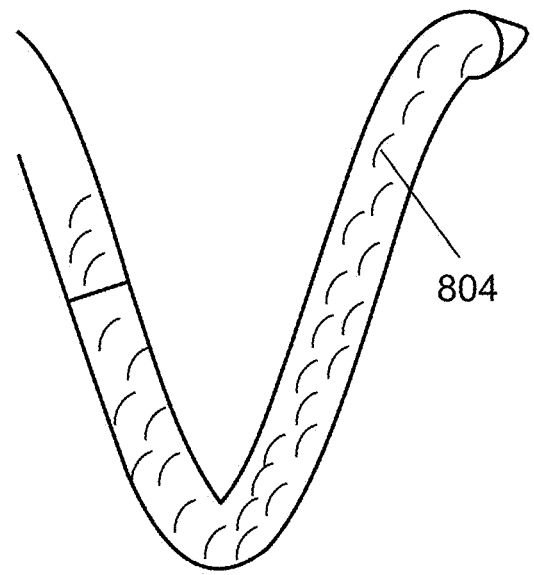

In some embodiments, a material from which a repair element is formed of comprises a textured and/or modified surface. For example, as shown in FIG. 8A, a shaft 800 of a helical repair element may be formed with one or more indentations 802. Additionally or alternatively, the shaft comprises a different type of texturing, such as bumps 804, for example as shown in FIG. 8B. A potential advantage of a textured surface may include better adherence to the tissue, reducing movement of the repair element inside the tissue.

Various Configurations of Locking Elements of a Tissue Repair Apparatus

Figure 9:
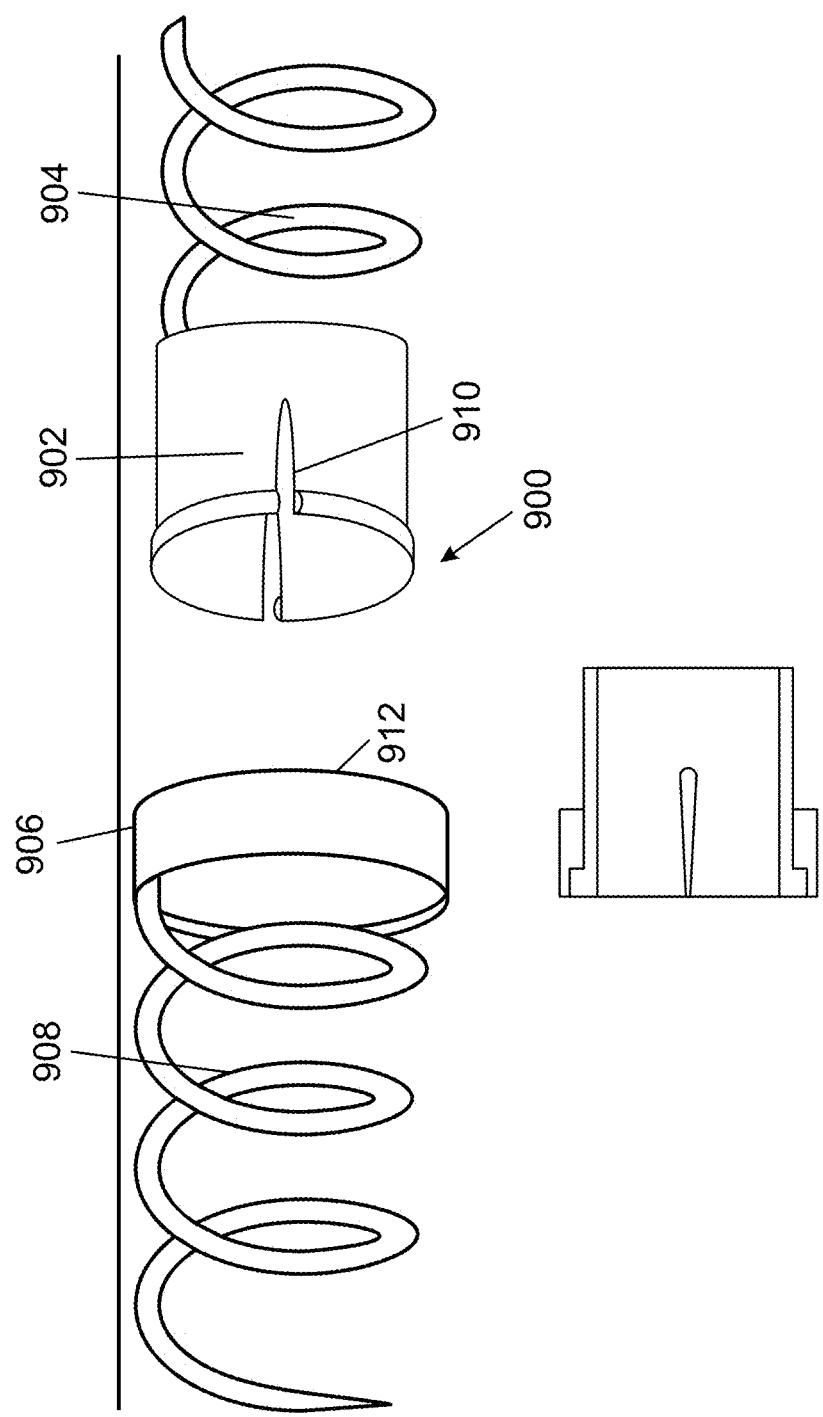
FIGS. 9, 10, 11 and 12 are various configurations of locking elements, according to some embodiments of the invention.

FIG. 9 shows a locking element 900 comprising a female connector 902, coupled to a proximal end of a first helical repair element 904, and a male connector 906, coupled to a proximal end of a second helical repair element 908, according to some embodiments of the invention.

In some embodiment, female connector 902 is shaped and/or sized to receive male connector 906. In the example shown herein, female connector 902 is cylindrically shaped to receive a rounded head 912 of male connector 906.

In some embodiments, female connector 902 is configured for slightly deforming in order to receive male connector 906, for example by comprising one or more slots such as slot 910 extending from the proximal end face of female connector 902 in a distal direction. Optionally, female connector 902 is formed of an elastic material so that when male connector 906 is fully received within female connector 902, a proximal end of female connector 902 slightly closes over the received male connector.

In some embodiments, axial rotation of the repair elements 906 and 904 is enabled by locking element 900, as male connector head 912 is free to rotate within the shaft of female connector 902 or vice versa.

Figure 10:
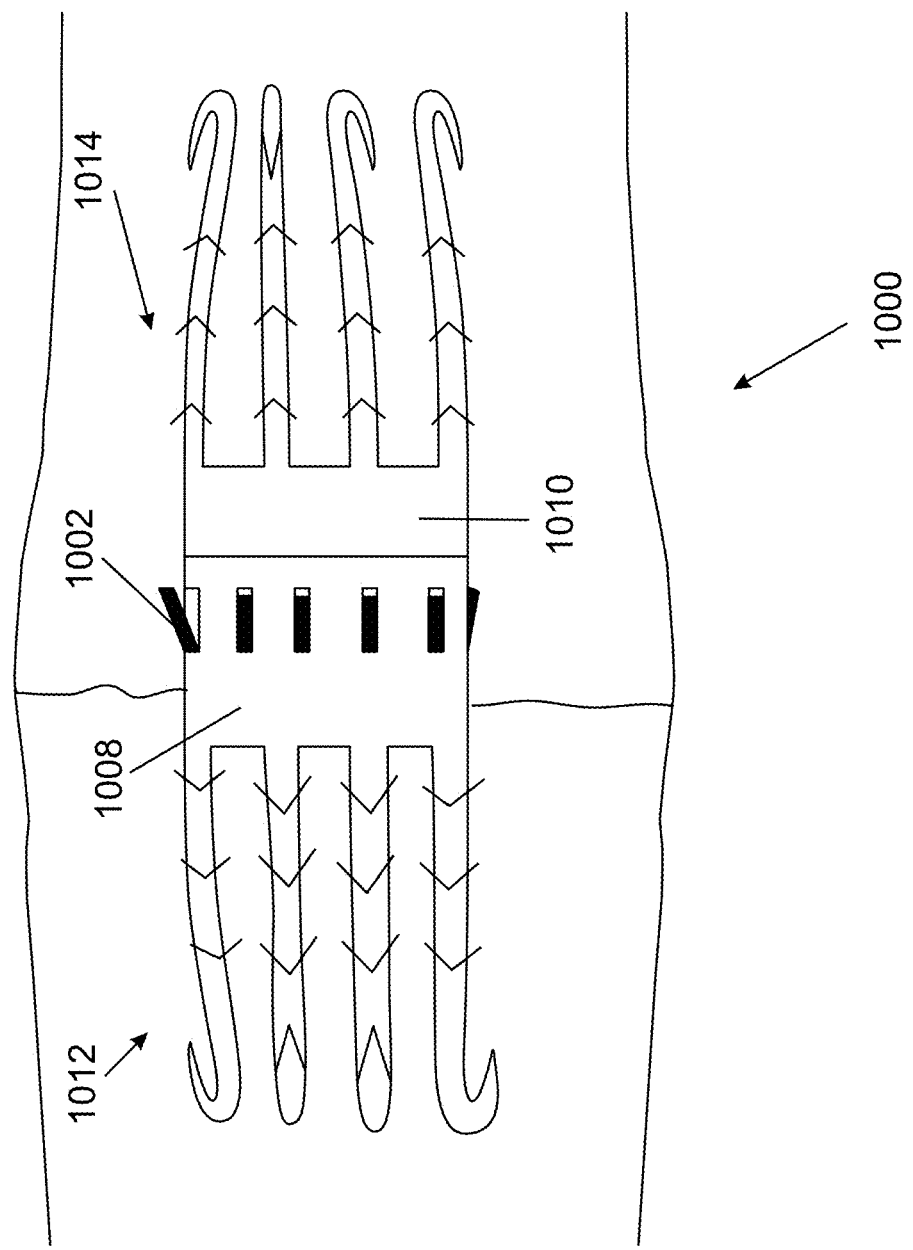

FIG. 10 shows an exemplary locking element 1000 comprising one or more snap-on tabs 1002, according to some embodiments of the invention. In some embodiments, a first connector 1008 of locking element 1000 comprises one or more slots 1004, in which one or more respective tabs 1002 configured on a second connector 1010 are received. Optionally, the arrangement of the slots and received tabs is configured to connect between repair elements 1012 and 1014 in a certain orientation, for example so that one or both of the elements are axially rotated until a desired alignment is obtained, and only then connectors 1008 and 1010 are attached to each other by insertion of the snap-on tabs 1002 into the respective slots 1004. A potential advantage of a locking element configured to couple between the repair elements at a certain orientation only may include the ability to connect the elements without vision, for example by the physician.

Figure 11:
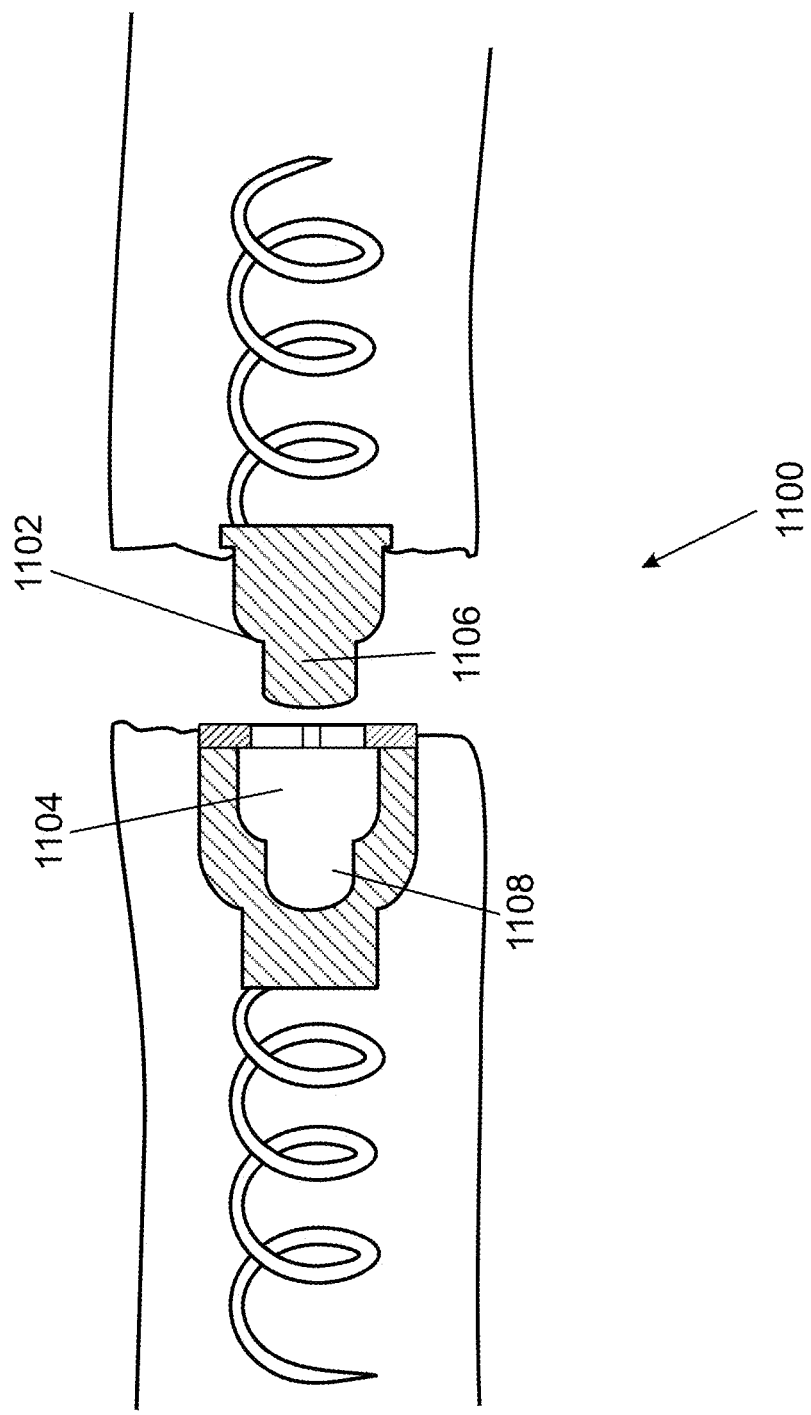

FIG. 11 is another exemplary configuration of a locking element 1100 comprising a male connector 1102 received within a female connector 1104, according to some embodiments of the invention. In some embodiments, a protrusion 1106 of male connector 1104 is shaped and/or sized to fit within a recess 1108 of female connector 1104 in a certain orientation. Optionally, protrusion 1106 and recess 1108 comprise matching profiles. A shape and/or size of the protrusion and matching recess may be selected to align the repair elements with respect to each other. Optionally, the matching profiles are selected so that movement of the repair elements with respect to each other, such as axial rotation and/or articulation, is limited to a certain extent. In some embodiments, connectors 1102 and 1104 are rotatably locked into each other.

Figure 12:
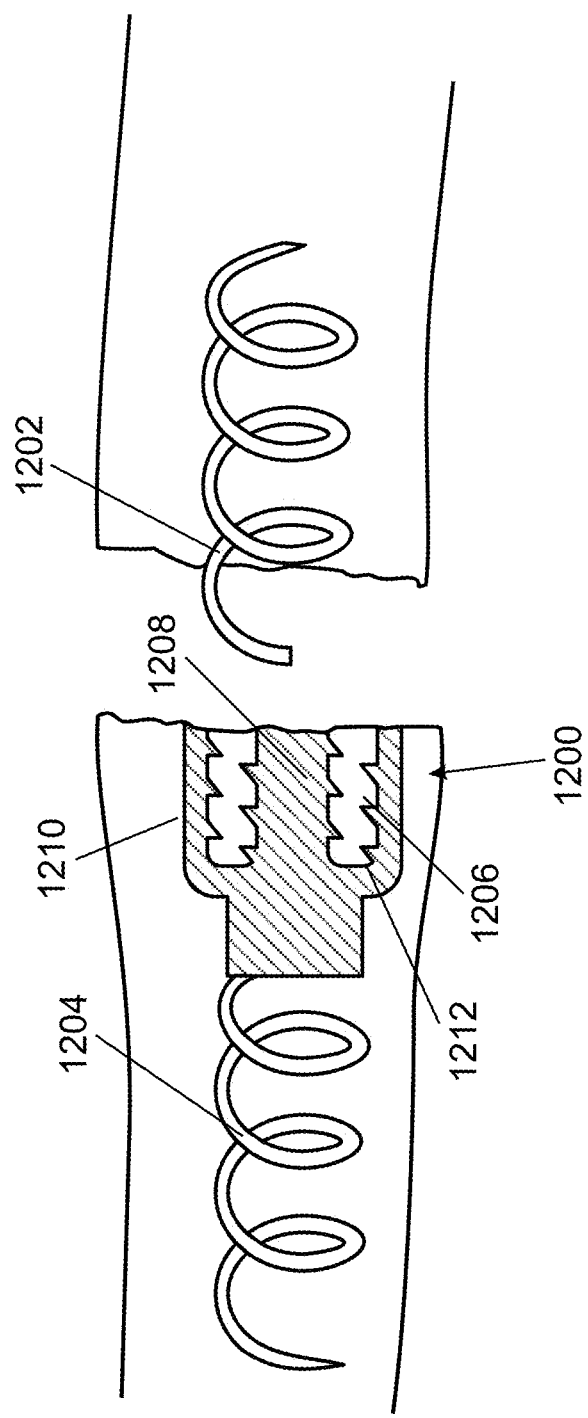

FIG. 12 shows a locking element comprising a single connector 1200 configured for receiving a proximal end of repair element 1202, according to some embodiments of the invention. In some embodiments, only one repair element 1204 comprises a connector 1200 at its proximal end. As shown in this example, connector 1200, shown at a transverse cross section, comprises a cylindrical shaft 1210 formed with a recess 1206 having a circular profile for receiving repair element 1202. Optionally, a proximal end of repair element 1202 is received within recess 1206 such that it is winded around a core 1208 of the connector shaft. In some embodiments, the outer walls of core 1208 and/or the inner walls of shaft 1210 facing recess 1206 comprise one or more teeth 1212 for restraining the shaft of repair element 1202 that is received within the recess.

In some embodiments, to reduce the risk of repair element 1202 disengaging connector 1200, for example by slipping out of shaft 1210, connector 1200 is crimped, squeezing the proximal end of repair element 1204 that is received within it. Optionally, crimping is obtained by applying force in a radially inwards direction on connector 1202, for example by pliers.

In some embodiments, shaft 1210 can be rotated with respect to repair element 1204. Optionally, the rotation allows for adjusting a distance between the shaft 1210 and a distal end of repair element 1204, without affecting the tendon.

In some embodiments, shaft 1210 can be used without core 1208. Alternatively, core 1208 can be used without shaft 1201, by winding the proximal end of repair element 1202 around it in a way that it is caught between the teeth.

Exemplary Repair Elements Positioned within a Ruptured Tendon

Figure 13A:
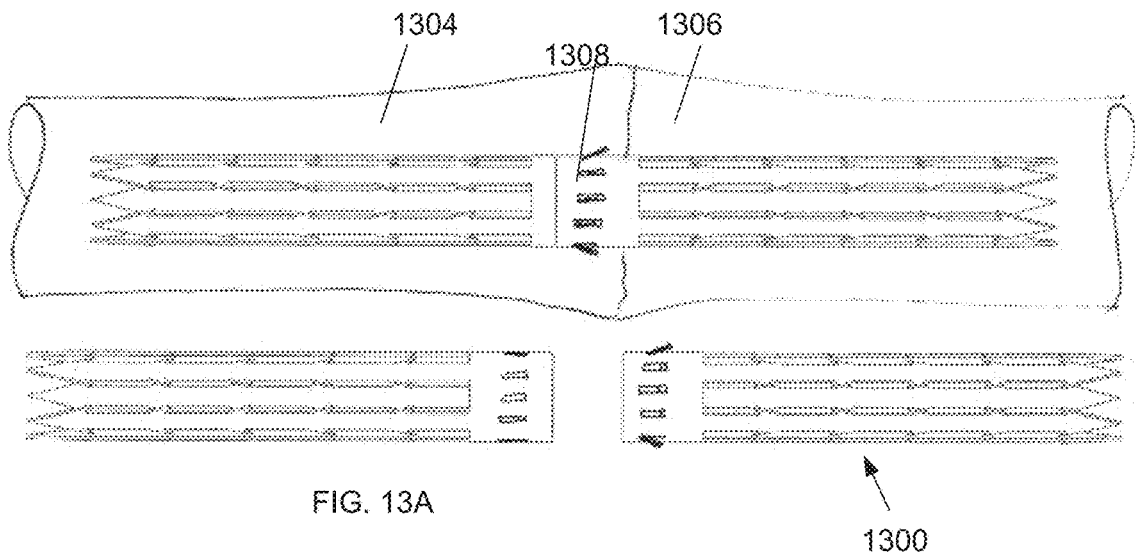
FIGS. 13A-B show multiple-strand repair elements coupled by a snap-fit mechanism locking element positioned within two portions of a tendon, according to some embodiments of the invention.
Figure 13B:
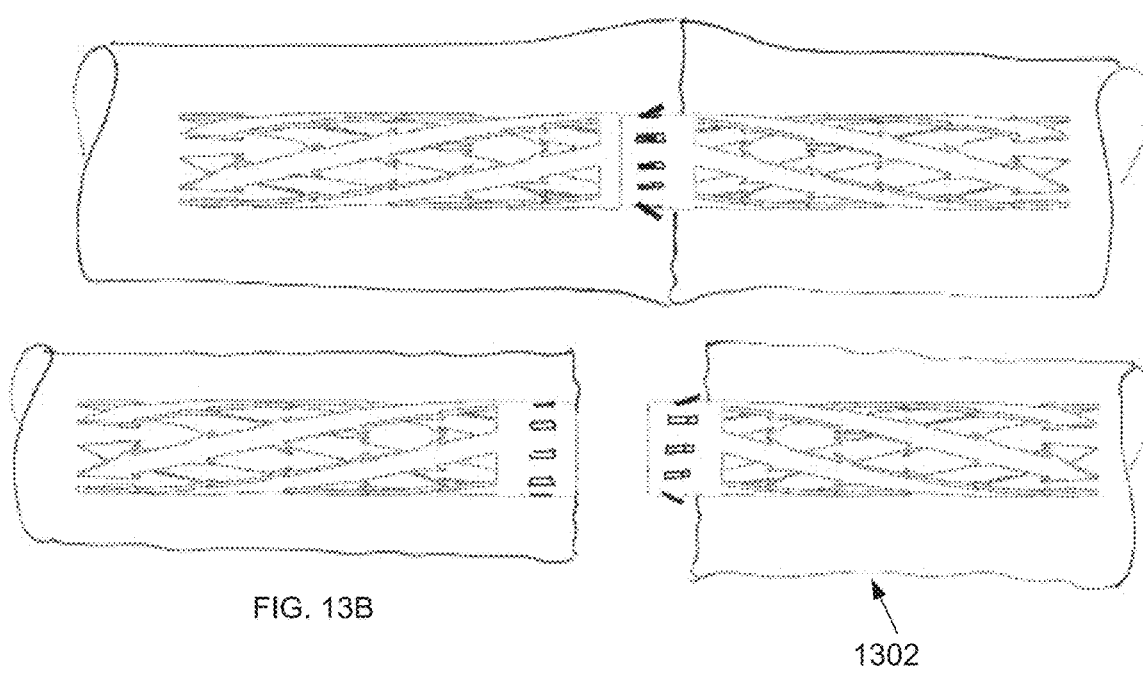

FIG. 13A-B show exemplary multiple-strand repair elements coupled to each other by a locking element comprising a snap-on mechanism, according to some embodiments of the invention. FIG. 13A shows repair elements 1300 comprising a plurality of strands arranged in parallel to a central axis of the repair element, before and after connecting the two tendon portions 1304 and 1306 by the snap-on locking element 1308. FIG. 13B shows repair elements 1302 comprising a plurality of winding strands, before and after connecting the two tendon portions by the snap-on locking element 1308.

Figure 14A:
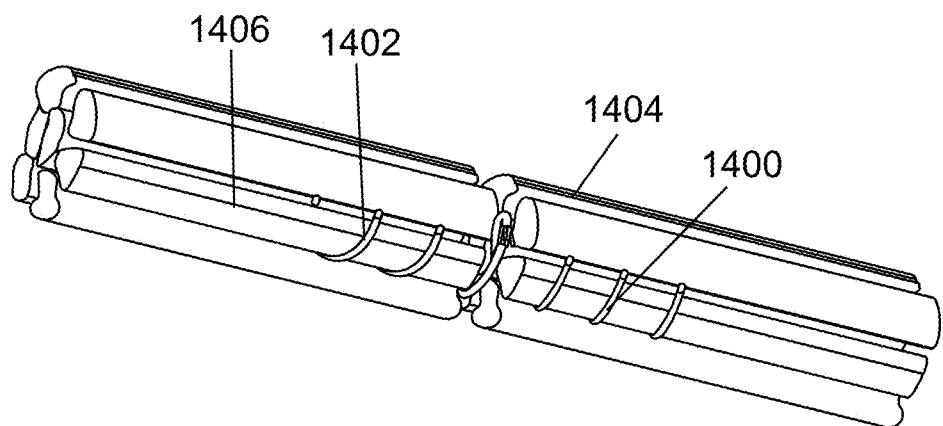
FIGS. 14A-C show helical repair elements inside two portions of a tendon, according to some embodiments of the invention.
Figure 14B:
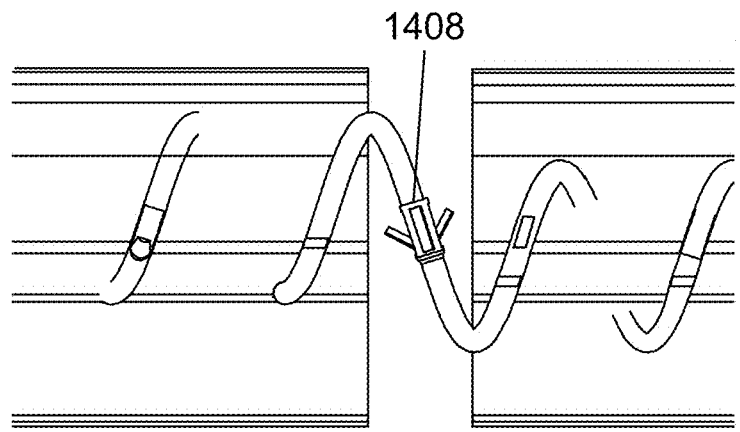
Figure 14C:
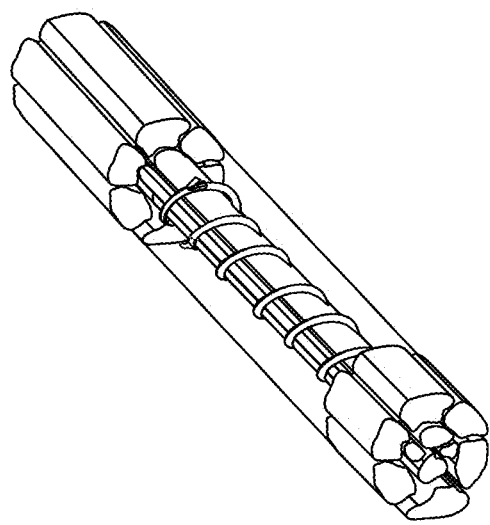

FIG. 14A-C show helical repair elements 1400 and 1402 inserted within a first tendon portion 1404 and a second tendon portion 1406 respectively. The two helical elements are connected by a locking element 1408 comprising a slot and respective tab, for example as shown in FIG. 14B.

In some embodiments, a locking element 1408 is a continuing portion of the helical element, for example configured on a shaft portion which continues the helical profile of the repair element. Alternatively, in some embodiments, the locking element is configured otherwise, for example being aligned with a longitudinal axis of the repair element, positioned substantially at the center of a cross section of the helical element.

Figures 15A, 15B:
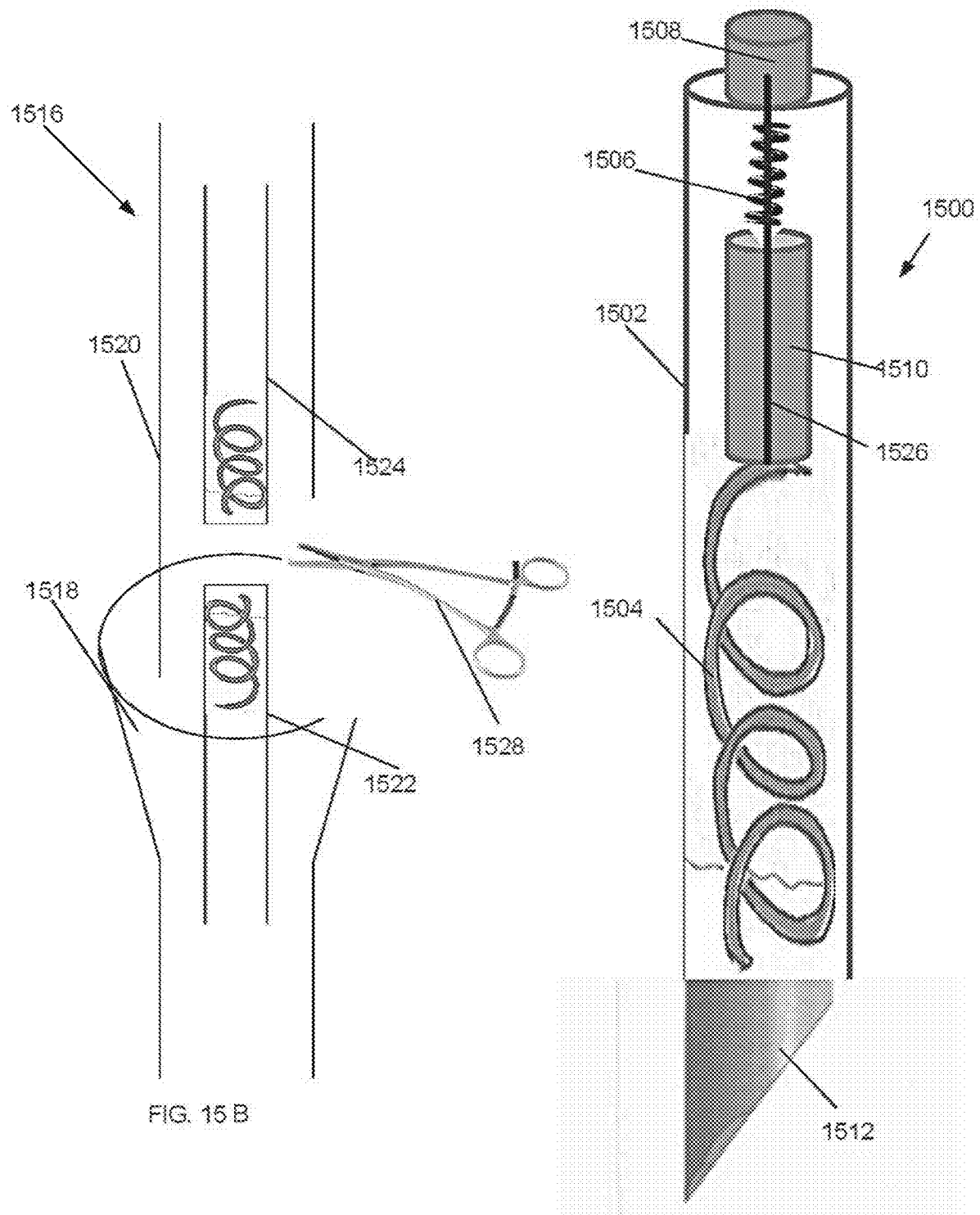
FIGS. 15A-B are a delivery device and a gripping device for use with a tissue repair apparatus, according to some embodiments of the invention.

Exemplary Delivery Device and Gripping Device for use with a Tissue Repair Apparatus FIG. 15A shows a delivery device 1500 for a tissue repair element, according to some embodiments of the invention. In some embodiments, the delivery device comprises a shaft 1502 comprising a tissue repair element 1504. Optionally, repair element 1504 is loaded onto shaft 1502, for example before introducing the element into the ligament portion. Alternatively, device 1500 is disposable, and repair element 1504 is comprised with the shaft, for example pre-loaded into the shaft during manufacturing. In some embodiments, delivery device 1500 comprises a "click-pen" like mechanism, for example including an elastic element such as spring 1506 and a pushable knob 1508, configured at proximal end of shaft 1502, to be engaged by a user and/or other tool. Optionally, pushing knob 1508 compresses spring 1506 against plunger 1510, which in turn forces repair element 1504 out of a distal end 1512 of shaft 1502 and into the tendon portion. In some embodiments, distal end 1512 is formed with a tapered tip, to facilitate introducing the repair element into the tendon.

In some embodiments, delivery device 1500 is forced manually into the tendon. Additionally or alternatively, an additional device (not shown in figure) is positioned coaxially to the tendon, and is configured to hold the tendon in place while device 1500 is impinged into the tendon. Optionally, after repair element 1504 is securely positioned within the tendon, delivery device 1500 and/or additional device and/or an inner needle on which device 1504 is threaded over are removed from the tendon, for example by pulling them in a proximal direction.

In some embodiments, repair element 1504 is rotatably threaded into the tendon. This insertion method may be advantageous in cases where, for example, a helical repair element is used. Optionally, repair element 1504 is inserted directly into the tendon, without the aid of a delivery device. Alternatively, delivery device 1500 comprises means for rotating repair element 1504 to thread it into the tissue. In an example, knob 1508 is configured for rotating element 1504, for example by being coupled to a shaft 1526 which is attached at its proximal end to knob 1508, and at its distal end to repair element 1504.

In some embodiments, repair element 1504 is advanced by step-wise clicking of knob 1508. Optionally, each time the knob is pushed in a distal direction, for example by a user, repair element 1504 is incrementally advanced in a distal direction within the shaft, until being forced out through distal end 1512.

FIG. 15B shows a gripping device 1516 suitable for holding the two tendon portions together and/or for approximating the proximal ends of the portions to attach them together, according to some embodiments of the invention. In some embodiments, gripping device 1516 comprises two parts, such as portion 1518 and portion 1520, which can be coupled to each other to sleeve-like configuration. Optionally, portion 1518 is formed with a larger opening at a proximal end, for example a funnel shaped opening as shown herein, for receiving portion 1520 within it. In some embodiments, each portion of the gripping device is positioned to encompass a tendon portion. In some embodiments, by having cylindrical portion 1520 received within funnel shaped portion 1518, tendon portions 1522 and 1524 are brought closer to each other, and are held together by gripping device 1516. Optionally, gripping device 1516 reduces the need for holding the proximal tendon portions using tweezers or the like and/or for pinning the tendon portions in place for example using a needle. In some embodiments, a lumen defined by the portions of the gripping device, when assembled together, is large enough to provide access at least to the locking element, to couple the repair elements to each other.

In some embodiments, gripping device 1516 is configured to engage tendon portions 1522 and 1524 at a distance from their proximal ends, for example a distance ranging between 0.5-5 cm from the proximal ends of the tendon portions. Optionally, the distance is selected to sufficient for at least initially attaching the tendon portions to each other. Optionally, following initial attachment, device portions 1518 and 1520 are brought closer to each other, for example as shown in this figure, to complete the attachment of the tendon portions. In some embodiments, gripping device 1516 can be locked in various positions with respect to the tendon portions.

In some embodiments, gripping device 1516 is formed with one or more windows, providing access to the proximal ends of the tendon portions.

In some embodiments, additionally or alternatively to gripping device 1516, manual or tool-aided clamping of the tissue is performed. Optionally, scissors 1528 comprising a ratchet mechanism are used for holding the proximal ends of the tendon portions and for bringing them closer to each other.

An Exemplary Force vs. Deformation Behavior of a Tissue Repair Device

Figure 16A:
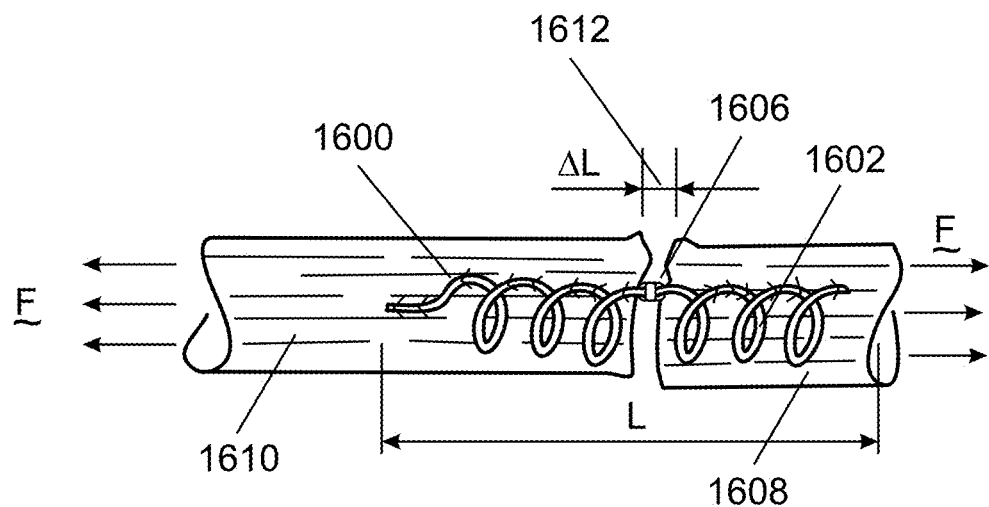
FIGS. 16A-B are a schematic force vs. displacement curve for a tendon repair apparatus, according to some embodiments of the invention.
Figure 16B:
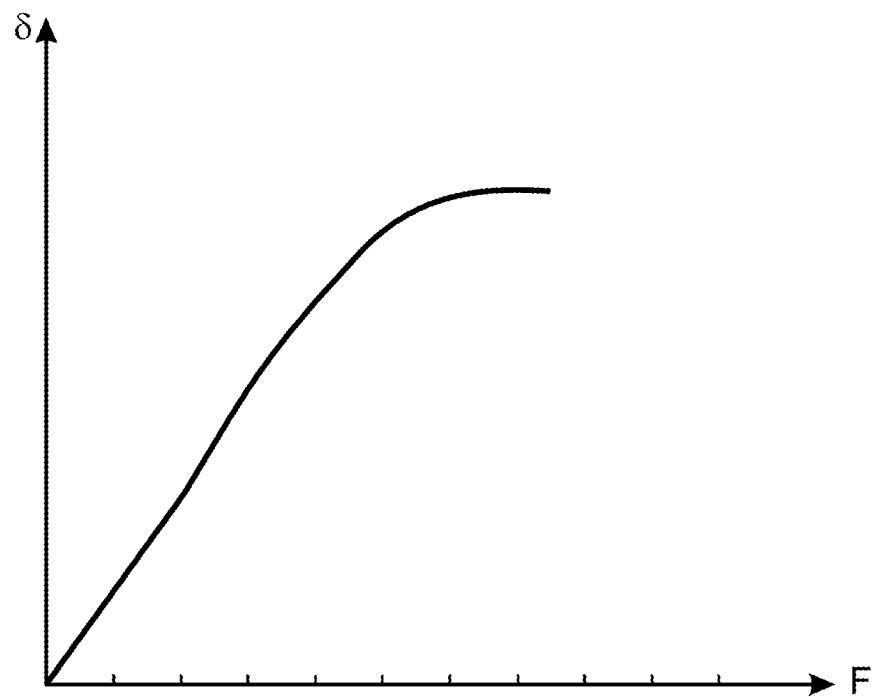

FIGS. 16A-B schematically illustrates a force vs. deformation curve, according to some embodiments of the invention. In some embodiments, as shown for example in FIG. 16A, pulling force F acts on the tendon portions in the distal directions. As a result, a deformation $\delta$ occurs in repair elements 1600 and 1602 which are connected by a locking element 1606. If the connected repair elements do not withstand the pulling force, they may be pulled away from each other, thereby causing the re-attached tendon portions 1608 and 1610 to disengage from each other. Therefore, in some embodiments, the repair elements 1600 and 1602 and/or locking element 1606 are configured to resist the pulling force at a level sufficient for maintaining the tendon portions attached to each other, for example having a stiffness k ranging between 2-15 N/mm, such as 5 N/mm, 9 N/mm, 12 N/mm or intermediate, larger or smaller values. Optionally, deformation $\delta$ is small enough so that no or significantly small gap.

1612, which does not have an effect on tendon function, is formed between the tendon portions.

It will be appreciated by persons skilled in the art that the present invention is not limited to what has been particularly shown and described hereinabove. Rather, the scope of the present invention includes both combinations and subcombinations of the various features described hereinabove, as well as variations and modifications thereof that are not in the prior art, which would occur to persons skilled in the art upon reading the foregoing description.

The terms "comprises", "comprising", "includes", "including", "having" and their conjugates mean "including but not limited to".

The term "consisting of" means "including and limited to".

The term "consisting essentially of" means that the composition, method or structure may include additional ingredients, steps and/or parts, but only if the additional ingredients, steps and/or parts do not materially alter the basic and novel characteristics of the claimed composition, method or structure.

As used herein, the singular form "a", "an" and "the" include plural references unless the context clearly dictates otherwise. For example, the term "a compound" or "at least one compound" may include a plurality of compounds, including mixtures thereof.

Throughout this application, various embodiments of this invention may be presented in a range format. It should be understood that the description in range format is merely for convenience and brevity and should not be construed as an inflexible limitation on the scope of the invention. Accordingly, the description of a range should be considered to have specifically disclosed all the possible subranges as well as individual numerical values within that range. For example, description of a range such as from 1 to 6 should be considered to have specifically disclosed subranges such as from 1 to 3, from 1 to 4, from 1 to 5, from 2 to 4, from 2 to 6, from 3 to 6 etc., as well as individual numbers within that range, for example, 1, 2, 3, 4, 5, and 6. This applies regardless of the breadth of the range.

Whenever a numerical range is indicated herein, it is meant to include any cited numeral (fractional or integral) within the indicated range. The phrases "ranging/ranges between" a first indicate number and a second indicate number and "ranging/ranges from" a first indicate number "to" a second indicate number are used herein interchangeably and are meant to include the first and second indicated numbers and all the fractional and integral numerals therebetween.

As used herein the term "method" refers to manners, means, techniques and procedures for accomplishing a given task including, but not limited to, those manners, means, techniques and procedures either known to, or readily developed from known manners, means, techniques and procedures by practitioners of the chemical, pharmacological, biological, biochemical and medical arts.

As used herein, the term "treating" includes abrogating, substantially inhibiting, slowing or reversing the progression of a condition, substantially ameliorating clinical or aesthetical symptoms of a condition or substantially preventing the appearance of clinical or aesthetical symptoms of a condition.

It is appreciated that certain features of the invention, which are, for clarity, described in the context of separate embodiments, may also be provided in combination in a single embodiment. Conversely, various features of the invention, which are, for brevity, described in the context of a single embodiment, may also be provided separately or in any suitable subcombination or as suitable in any other described embodiment of the invention. Certain features described in the context of various embodiments are not to be considered essential features of those embodiments, unless the embodiment is inoperative without those elements.

What is claimed is:

1. An apparatus for coupling first and second elongate tissue portions of a subject, comprising:
   first and second repair elements, each said repair element comprising:
   a distal end configured for insertion into a respective one of said first and second tissue portions;
   an elongated body configured to extend axially within said respective one of said first and second tissue portions and to engage tissue in said respective one of said first and second tissue portions, said elongated body defining a hollow to encompass a part of the respective one of said first and second tissue portions, wherein said elongated body comprises a helical portion; and
   a proximal end;
   wherein said distal end of each said first and second repair elements is rigid enough to be helically advanced into the respective one of the first and second tissue portions, in an axial direction, by force exerted on a respective one of said first and second repair element proximal ends to axially couple the first and second tissue portions, said helical portion of each of said first and second repair element rigid enough to retain a helical configuration while being advanced into the respective one of said first and second tissue portions; and wherein each of said first and second repair elements comprises a connector portion at its proximal end, at least one of said connector portions being integrally formed with a respective one of said first and second repair elements, said connector portions configured for coupling said proximal end of said first repair element to said proximal end of said second repair element such that said repair element proximal ends abut each other, to attach between said first and second tissue portions.

2. The apparatus according to claim 1, wherein said connector portions are shaped with matching profiles to connect to each other, wherein one of said connector portions is a female connector portion formed with a plurality of slots, and the other of said connector portions is a male connector portion formed with a plurality of tabs configured to snap into said slots of said female connector portion upon connection.

3. The apparatus according to claim 1, wherein said connector portions are shaped with matching profiles to connect to each other, wherein one of said connector portions is a female connector portion and the other of said connector portions is a male connector portion, said male connector portion comprising a projection and said female connector portion comprising a recess, said projection and recess formed with matching profiles suitable for defining an orientation of said first repair element with respect to said second repair element.

4. The apparatus according to claim 1, wherein said connector portions are shaped with matching profiles to connect to each other, wherein said connector portions comprise a female connector portion configured for receiving a male connector portion, said female connector portion comprising one or more axially extending slots to be elastically deformed when receiving a projection of said male connector portion.

5. The apparatus according to claim 1, wherein said connector portions are shaped with matching profiles to connect to each other, wherein a first one of said connector portions projects externally to a proximal end of the first tissue portion, and a second one of said connector portions is embedded within a proximal end of the second tissue portion, wherein said connector portions overlap each other when connected.

6. The apparatus according to claim 1, wherein said connector portions are each positioned at a non-axial location with respect to the respective one of said first and second elongate tissue portions.

7. The apparatus according to claim 1, wherein a diameter of each said connector portion is smaller than a diameter of the respective one of said first and second tissue portions by at least 10%.

8. The apparatus according to claim 1, wherein a diameter of each said helical portion of each of said first and second repair elements ranges between 50% to 75% of a diameter of the respective one of the first and second elongate tissue portions.

9. The apparatus according to claim 1, wherein a said helical portion of each of said first and second repair elements is formed with a textured external surface.

10. The apparatus according to claim 1, wherein, when said proximal end of said first repair element is coupled to said proximal end of said second repair element, said helical portions are continuous.

11. The apparatus according to claim 1 wherein, in a coupled orientation, said proximal ends of said first and second repair elements are oriented non-axially with respect to said coupled first and second repair elements.

12. The apparatus according to claim 1, wherein each of said hollows of said first and second repair elements defines an axis and wherein, when in a coupled orientation, said hollows of said first and second repair elements are adjacent to each other and are coaxial.

13. The apparatus according to claim 1, wherein each of said repair elements has a stiffness ranging from 2-15 N/mm.

14. The apparatus according to claim 1, wherein the first and second elongate tissue portions are tendon portions.

15. The apparatus according to claim 1, wherein each of said repair elements comprises a plurality of axially extending strands configured to engage the respective one of said first and second elongate tissue portions, said strands arranged in a cylindrical configuration.

16. The apparatus according to claim 15, wherein said strands are formed of a shape memory alloy.

17. The apparatus according to claim 15, wherein said strands of each of said repair elements are winded with respect to a longitudinal axis of the respective one of each of said repair elements.

18. The apparatus according to claim 15, wherein said strands of each of said repair elements occupy between 5% and 25% of a cross sectional area of the tissue in the respective one of said first and second tissue portions.

19. The apparatus according to claim 15, wherein said strands of each said repair element comprise elastic distal ends to be bended in a proximal direction for penetrating into the tissue in the respective one of said first and second tissue portions.

20. The apparatus according to claim 1, wherein a diameter of a shaft of each said helical portion of each of said first and second repair elements ranges between 3%-15% of a diameter of the respective one of the first and second elongate tissue portions.

21. The apparatus according to claim 20, wherein said shaft diameter is constant over at least 85% of a length of said shaft.

* * * * *